United States Patent [19]

Ward et al.

[11] Patent Number: 4,687,732

[45] Date of Patent: Aug. 18, 1987

[54] VISUALIZATION POLYMERS AND THEIR APPLICATION TO DIAGNOSTIC MEDICINE

[75] Inventors: David C. Ward, Guilford; Jeffry J. Leary, East Haven, both of Conn.; David J. Brigati, Hershey, Pa.

[73] Assignee: Yale University, New Haven, Conn.

[21] Appl. No.: 503,298

[22] Filed: Jun. 10, 1983

[51] Int. Cl.[4] .................. G01N 33/53; G01N 33/533; G01N 33/534; G01N 33/535

[52] U.S. Cl. .......................................... 435/6; 435/7; 435/14; 435/21; 435/25; 435/28; 435/188; 435/810; 436/501; 436/504; 436/537; 436/545; 436/546; 436/800; 436/801; 436/804; 436/808; 436/827

[58] Field of Search ............... 436/537, 801, 803, 827, 436/501, 504, 545, 546, 800, 804, 808; 435/6, 7, 14, 21, 25, 28, 188, 810

[56] References Cited

U.S. PATENT DOCUMENTS

| | | | |
|---|---|---|---|
| 3,690,834 | 9/1972 | Goldstein | 436/537 |
| 3,996,345 | 12/1976 | Ullman | 436/537 |
| 4,174,384 | 11/1979 | Ullman | 436/537 |
| 4,220,450 | 9/1980 | Maggio | 436/537 |
| 4,220,722 | 9/1980 | Rowley | 436/537 X |
| 4,228,237 | 10/1980 | Hevey | 435/7 |
| 4,289,747 | 9/1981 | Chu | 435/7 X |
| 4,358,535 | 9/1982 | Falkow | 435/6 X |
| 4,373,932 | 2/1983 | Gribnau | 435/7 X |
| 4,434,150 | 2/1984 | Azad | 435/7 X |

OTHER PUBLICATIONS

Langer, P. R. et al., Proc. Natl. Acad. Sci. USA, 78 (11), 6633–6637, (Nov. 1981).

Primary Examiner—Sidney Marantz
Attorney, Agent, or Firm—James F. Haley, Jr.

[57] ABSTRACT

A method for detecting a minute quantity of an inorganic or organic target molecule by combining it with a composition of a detecting agent for the target molecule which carries, by direct or indirect means, a visualization polymer. The visualization polymer is composed of multiple units of a visualization monomer which are covalently linked together directly or indirectly covalently linked together by coupling agents which bond to chemical groups of the monomer. The monomer may be an enzyme, a tagged polypeptide, a tagged polyol, a tagged polyolefin or a tagged carbohydrate. The detecting agent may be an antibody, an enzyme, a lectin, strand of a DNA receptor protein, avidin, streptavidin and the like. The visualization polymer produces a high degree of amplification for the detection of the target molecule.

45 Claims, 7 Drawing Figures

VISUALIZATION POLYMERS AND THEIR APPLICATION TO DIAGNOSTIC MEDICINE

BACKGROUND OF THE INVENTION

The invention relates to methods for medicinal diagnosis and to substances for obtaining such diagnoses. More specifically, the substances are visualization polymers of molecules such as proteins, enzymes, and chemically tagged polyols, polyolefins, carbohydrates and natural or synthetic polypeptides, which can be combined with biological material and provide substantial chemical amplification of the quantity of material detected.

The requirements for a medical diagnostic method, which detects and/or quantifies the presence of biological material, include identification of extremely small quantities and selection of a single species of material from a complex mixture containing similar species. In the past, such methods as radiolabeling, radiobioassay and immunoassay techniques have formed the basis for such diagnostic medicine. For example, immunological reagents have been used extensively for detecting and/or quantitating a broad spectrum of molecular species such as proteins, lipids, carbohydrates, steroids, nucleic acids, drugs, carcinogens, antibiotics, inorganic salts etc. Indeed, polyvalent and monoclonal antibodies are very important diagnostic tools in most areas of clinical medicine today.

During the past 40 years, a variety of procedures have been developed to visualize specific antigen-antibody interactions fluorimetrically or colorimetrically. Since the utility of immunodiagnostic procedures often depends upon the sensitivity and the specificity with which the target antigen or molecule can be detected, new methods for increasing these detection parameters are highly desirable. The scientific and patent literature is replete with work designed with this goal in mind. A detailed discussion of the advantages and disadvantages of immunologic methods can be found in any standard textbook on immunocytochemistry; see for example, L. A. Sternberger, "Immunohistochemistry", 2nd Ed., John Wiley and Sons, New York, 1979.

Immunologic detection methods can utilize direct or indirect visualization techniques for measurement of the formed immune complex. In general, these methods visually indicate the presence of the complex through use of an entity coupled to the complex which produces a detectable, quantifiable signal such as color, fluorescence, radioactivity, enzymatic action and the like. The more signal intensity present per complex, the better will be the sensitivity for the presence of a minute quantity of target molecule.

Of these methods, the simplest and least sensitive is direct immunofluorescence. In this method, a primary antibody (or specific ligand-binding protein) is chemically linked to a fluorochrome, such as rhodamine or fluorescein which functions as the signal entity.

Indirect immunofluorescence methods, in which a primary antibody is used unmodified and it, in turn, is detected with a fluorescently-labeled secondary antibody, generally will increase the detection sensitivity about two to four-fold over direct methods. An additional three to five-fold enhancement in sensitivity has been reported using a "haptene-antibody sandwich" technique; see Cammisuli, et al., J. Immunol., 117,1695 (1976); Wallace, et al., J. Immunol Methods, 25, 283 (1979). According to this technique, ten to fifteen molecules of a small haptene determinant such as 2,4-dinitrophenol are chemically coupled to each primary antibody molecule. Then, by use of a fluorescently-labeled second antibody which complexes with the haptene molecules, rather than with the primary antibody itself, more of the secondary visualization protein can be bound per antigen site, thus further increasing the sensitivity.

Nakane and associates; see Nakane, et. al., J. Histochem. Cytochem., 22, 1084 (1974), Wilson, et. al. "Immunofluorescence and Related Staining Techniques", W. Knapp, H. Holuban and G. Wick, Eds. Elsevier/North-Holland Biomedical Press, p. 215; have coupled secondary antibodies to monomeric horseradish peroxidase and used the catalytic activity of peroxidase enzyme to reveal either the site, or the amount, of antigen in the test sample. Similar enzymatic assays have been developed with intestinal or bacterial alkaline phosphatase conjugated secondary antibodies; see Avrameas, Immunochemistry, 6, 43, (1969); Mason, et. al., J. Clin. Path., 31, 454 (1978).

The enzymatic signal of this method may occur in either of two ways. Enzymatic conversion of a soluble enzyme substrate into an *insoluble*, colored product permits the direct localization of the antigen by direct macroscopic visualization or by light microscopic examination. Alternatively, colorless substrates can be enzymatically converted into *soluble* colored products which can be used to quantitate antigen concentrations by direct colorimetric analysis. The latter method is the basis of the Enzyme-Linked Immuno-Sorbent Assay (ELISA), which is widely used in clinical laboratories around the world; see Sternberger, *Immunohistochemistry*, 2nd Edition, John Wiley and Sons, N.Y. (1979); Engvall, et. al., *Immunochem.*, 8, 871 (1972); Engvall, et al., *J. Immunol.*, 109, 129 (1972); Guesdon, et. al., *J. Histochem. and Cytochem.*, 27, 1131 (1979); Voller et. al., "The Enzyme Linked Immuno Sorbent Assay (ELISA)", Dynatech Laboratories Inc., Alexandria (1979).

These enzyme-based detection methods are generally more sensitive than direct or indirect immunofluorescence methods since the high turnover of substrate by the enzyme continuously accumulates a measurable product over long periods of time.

To further increase the sensitivity of immunoenzyme assays, Sternberger; see Sternberger, et. al. *J. Histochem, Cytochem.* 18, 315 (1970) developed a three stage peroxidase-antiperoxidase (PAP) assay method. Following the addition of a primary antibody and a secondary antibody, which acts as a bridge between the primary antibody and antiperoxidase antibody, a peroxidase-antiperoxidase antibody complex (PAP complex) is added to the sample prior to the development of the enzymatic reaction. Since the PAP complex contains two immunoglobulins (antiperoxidase antibodies) and three active peroxidase molecules, the net effect is to provide more enzyme at the antigen site with which to amplify the detection signal. Although quite useful, the PAP detection system has limitations. The secondary "bridge" antibody must be used at saturating levels to ensure optimal binding of the PAP complex. Furthermore, the antiperoxidase and the primary antibody must be of the same, or an immunologically cross-reacting, species so that the secondary antibody will bridge to both.

During the past few years it has been shown that the specific and tenacious interaction between biotin, a small water soluble vitamin, and avidin, a 68,000 dalton glycoprotein from egg white, can be exploited to develop antigen or ligand detection systems, see Bayer and Wilchek in Voller, et. al., "The Enzyme Linked Immuno Sorbent Assay (ELISA)", Dynatech Laboratories Inc., Alexandria (1979). Biotin can be covalently coupled to amino, carboxyl, thiol or hydroxyl groups present in proteins, glycoproteins, polysaccharides, steroids and glycolipids using well established chemical reactions; see Guesdon, et. al., *J. Histochem. and Cytochem.*, 27, 1131 (1979); Sternberger, et. al., *J. Histochem. Cytochem.*, 18, 315 (1970); Bayer, et. al., *Methods Biochem. Anal.*, 26, 1, (1980); Bayer, et. al., *J. Histochem. Cytochem.*, 24, 933 (1976); Heitzmann, et. al., *Proc. Natl. Acad. Sci. USA*, 71, 3537 (1974). Biotin can also be introduced into other macromolecules, such as DNA, RNA and co-enzymes, by enzymatic methods that utilize biotin-labeled nucleotide precursors; see Langer, et al., *Proc. Natl. Acad. Sci. USA*, 78, 6633 (1981). Similarly, avidin can be coupled to a host of molecular species by standard chemical reactions; see Sternberger, "Immunohistochemistry", 2nd Edition, John Wiley and Sons, N.Y. (1979); Nakane, et. al., *J. Histochem. Cytochem.*, 22, 1084 (1974); Guesdon, et. al., *Histochem. and Cytochem.*, 27, 1131 (1979); Bayer et. al., *Methods Biochem. Anal.*, 26, 1, (1980). This allows for great flexability in designing detection systems for use in immunology, immunopathology and molecular biology.

In 1981 Hsu; see Hsu, et. al., *Amer. J. Clin. Path.*, 75, 734 (1981); Hsu, et al., *J. Histochem. Cytochem.*, 29, 577 (1981); reported the use of avidin-biotinylated horseradish peroxidase complex (ABC) for antigen detection. In their three-step procedure, the primary antibody incubation is followed by an incubation period with a biotin-labeled secondary antibody and then with the ABC complex, formed by preincubating avidin with a titrated amount of biotinylated peroxidase. Since avidin has four biotin-binding sites per molecule, at least three peroxidase enzymes can be added to avidin without interfering with its ability to interact with the biotinylated secondary antibody. Hsu and associates; see Hsu et. al., *Amer. J. Clin. Path.*, 75, 734 (1981); Hsu, et. al., *J. Histochem. Cytochem.*, 29, 577 (1981); reported that the ABC detection procedure was 4–8 times more sensitive in detecting antigens in tissues than either the immunoperoxidase or the PAP detection systems. Madri; see Madri, et. al., *Lab. Invest.*, 48, 98 (1983); has confirmed these observations and shown that the ABC method is four-fold more sensitive for antigen detection using an ELISA system than either the immunoperoxidase or the PAP techniques. By all criteria tested, the ABC method is the most sensitive detection procedure used in clinical diagnostic labs to date.

The limit of sensitivity for the ABC method, however, appears to be 30 to 100 pg of a target molecule such as a protein or nucleic acid. This is significantly higher than the upper limit required for detection of a single molecule per cell. Limits for other less sensitive methods are even higher. Accordingly, it is an object of the invention to develop visualization methods which substantially improve sensitivity over that provided by known visualization techniques. Yet another object is development of a stable, easily manipulated visualization system which has a long shelf life. Finally, as with any diagnostic technology, an ultimate goal would be development of a capacity for detecting a single molecule of a species in any given cell.

SUMMARY OF THE INVENTION

These and other objects are achieved by the invention which is directed to a method for visualizing the presence of an inorganic or organic target molecule, a visualization polymer and a detection-visualization complex used in this method and a detection kit for accomplishing practise of the method.

According to the invention, the presence of a target molecule may be visualized by combining it with a visualization polymer of multiple visualization units covalently linked together by polymerization or a coupling agent. The target-polymer combination is accomplished through the intermediacy of a detecting agent which is selective for the target molecule and carries the visualization polymer.

The visualization polymer provides substantial chemical amplification of the quantity of target molecule detected. Each unit of the polymer possesses at least one visualization site and the units are linked in a manner which preserves the intrinsic activity of the visualization sites of the units. A visualization unit can generate or produce color, fluorescence, luminescence, localization of radioactivity or localization of electron dense material. The units may be selected from an enzyme or a tagged natural or synthetic polypeptide, a tagged polyol, tagged polyolefin, or a tagged carbohydrate.

The units are directly linked by polymerization or indirectly linked by a coupling agent. Direct polymerization or agent coupling bonds chemical groups or unit backbone moieties of adjacent units. The chemical groups or backbone moieties utilized for each unit of polymer will be independently selected from an amine group, an oxidized form of a 1,2-diol group, a carboxy group, a mercaptan group, a hydroxy group or a carbon-hydrogen bond.

Preservation of unit visualization site activity is obtained by forming polymerization bonds or linking chemical groups or backbone moieties of the units which are at least one atom away from the visualization site. This may be determined by preparing a visualization polymer with each type of coupling agent or with each type of direct polymerization process and testing to determine whether additive activity has been produced. Alternatively, if the overall chemical structure of the visualization site can be determined, unit moieties which do not form part of this structure may be linked by the coupling agent or polymerization process. For instance, if the site is analyzed and found to contain glycine, serine and histidine but not lysine or a sugar, lysine or a sugar may be used as the chemical group for linking.

The visualization sites of the units can be sites of biological activity. For example, sites for enzymatic action will provide visualization when reacted with an appropriate substrate. In this manner, the visualization sites can be utilized to generate soluble or insoluble bodies of color, fluorescence, luminescence, radioactivity or high electron density which can be measured and correlated with the quantity of target molecules detected.

The sites may also be created chemically. Combining a natural or synthetic polypeptide, polyol, polyolefin or carbohydrate with a visualization tag selected from a fluorescent chemical group, a dye, a radioactive group, a photon emitter (a luminescent group) or an electron dense moiety will produce monomer units which can be visualized. The tag may be present at an equivalent ratio relative to each unit. It is preferred, however, to have a multiple number of tags per unit.

The units of the visualization polymer are joined together by direct polymerization process bonding or by coupling agent linking. Direct polymerization produces interbonding of available chemical groups or backbone moieties in adjacent units. For example, oxidative enzymes such as horseradish peroxidase can be used to polymerize monomer units by oxidative cross-linking.

Alternatively, a coupling agent, derived from a bifunctional or multifunctional organic cross-linking reagent, bonds with the appropriate chemical group or backbone moiety of the units. In this context the term "coupling agent" denotes the linkage group after bonding and the term cross-linking reagent denotes the linkage compound before bonding.

The cross-linking reagent has generic formula I:

Reactive groups A, B and E of formula I are independently selected from hydrogen, a carboxylic acid group, an acid halide, an activated ester, a mixed anhydride, an acyl imidazole, an N-(carbonyloxy)imide group, an iminoester, a primary amine, an aldehyde group, an alphahalomethylcarbonyl group, a hydrazine group, an acyl hydrazide group, an azide group or an N-maleimide group. At least two of A, B and E are other than hydrogen. Multifunctional cross-linking reagents, with more than three reactive groups which are similar to A, B and E, are also within the scope of the invention. These additional reactive groups will be independently selected from the foregoing definitions of A, B and E.

$R^1$ of formula I is an aliphatic group of at least two carbons or an aromatic group of at least six carbons.

Choice of the reactive groups of formula I will depend upon the selection of the chemical groups or backbone moieties of the units which are to be linked. Each kind of chemical group or backbone moiety will react with its corresponding appropriate reactive group or groups of formula I. An amine group will react with a carboxylic acid group, an acid halide, an activated ester, a mixed anhydride, an acyl imidazole, an N-(carbonyloxy)imide group, an iminoester, an azide or an aldehyde group. An oxidized 1, 2-diol group (a dialdehyde) will react with a primary amine, a hydrazine group, an azide or an acyl hydrazide group. A carboxy group will react with a primary amine, a hydrazine group, an azide or an acyl hydrazide group. A mercaptan group will react with an alphahalomethylcarbonyl group or an N-maleimide group. An hydroxy group will react with a carboxylic acid group, an acid halide, an activated ester, a mixed anhydride, an acyl imidazole or an N-(carbonyloxy)imide. A carbon-hydrogen bond will react with an azide (nitrene).

According to the method of the invention, there is utilized a detecting agent which is specific for the target molecules. The agent directly or indirectly carries the visualization polymer to the target. The detecting agent may be an antibody, a lectin, a DNA repressor protein, a stereospecific receptor-protein, a high affinity enzyme, a sequence specific polynucleotide binding protein, avidin, streptavidin, a hormone or a complementary polynucleotide sequence.

The detecting agent may carry the visualization polymer by direct covalent bonding with the polymer, or indirect bonding through an intermediate covalent bonding group. The detecting agent may also carry the polymer through an intermediate ligand binding complex which arrangement may be direct or indirect. In the direct arrangement, the agent acts as a ligand binding compound also and the corresponding ligand is covalently bonded to the visualization polymer. In the indirect arrangement, a first ligand is bound to the agent, a second ligand is bound to the polymer and they are sandwiched with a ligand binding compound such that the first and second ligands function as bridges complexing with the compound.

Ligand binding compounds include an antibody, lectin, avidin, streptavidin, a high affinity enzyme, a sequence specific polynucleotide binding protein or a complementary polynucleotide sequence. Ligands will be the appropriate ones forming complexes with each type of compound. They include antigen, specific sugar, biotin, iminobiotin, specific substrate, polynucleotide and complementary polynucleotide respectively.

A preferred detecting agent-visualization polymer carrying arrangement according to the invention is the indirect arrangement wherein the detecting agent is an antibody, a complementary polynucleotide sequence or is a lectin; the ligand binding compound is avidin or streptavidin, and the first and second ligands are independently selected from biotin or iminobiotin, N-(omega alkanoyl) amido [biotin or iminobiotin] wherein the alkanoyl group is 4 to 20 carbons in length or and N-(omega-oligomer) amido [biotin or iminobiotin] wherein the oligomer is a polyol, polyamide or polyvinyl group of 2 to 30 units in length. A preferred ratio of visualization polymer to avidin or strepavidin in any of these ligand complexes is about 3 to 1.

In this preferred indirect arrangement, when the detecting agent is a lectin, the target molecule will be a corresponding appropriate sugar. When it is an antibody, the target molecule will be an antigen or haptene which complexes with that antibody. When it is a polynucleotide sequence, the target will be a complementary polynucleotide sequence which hybridizes with the agent.

A preferred method according to the invention utilizes the foregoing preferred indirect arrangement.

An especially preferred method for detection of target molecules is built upon the foregoing preferred arrangement; however, it employs a second bridging component. The complex, i.e., avidin or streptavidin-(biotin ligand)-visualization polymer, is used to complex with a biotin labelled second antibody. The second antibody is a general reagent for the first antibody detecting agent which in turn is specific for the target. The first antibody is incubated with the target to form an antigen-antibody conjugate. Then the second antibody is incubated with this conjugate. Following the second incubation, the visualization polymer complex is added which binds to the second antibody and provides visualization.

Yet another preferred method, according to the invention, also utilizes the preferred indirect complexing ligand arrangement. In this arrangement, the detecting agent is a complementary polynucleotide sequence and the target is the corresponding native polynucleotide sequence which will hybridize with the complementary sequence. The detecting agent and the visualization polymer are labeled with a biotin or iminobiotin group. A complex of avidin or streptavidin-(biotin ligand)-visualization polymer is formed. The labelled polynucleotide detecting agent is added to the complex biological mixture containing the native polynucleotide sequence to be detected. Hybridization is allowed to take place, then the complex is added which binds to the hybridized and labelled polynucleotide detecting agent and which provides visualization.

Especially preferred carrying arrangements include those of the two foregoing preferred methods.

The complexes between the ligand carrying compound and the visualization polymer bonded to the corresponding ligand are also included within the invention. These complexes are described above as part of the carrying arrangement of the invention.

Preferred detection methods and preferred visualization polymers include polymers having multiple units of an enzyme or multiple units of a natural or synthetic polypeptide or polyolefin chemically bonded to a tag selected from a fluorescent group, a dye, a luminescent group or an electron dense group. Preferred enzymes include alkaline phosphatase, peroxidase, galactosidase, glucose oxidase, acid phosphatase and luciferase. Preferred polypeptides include polyamides of dicarboxylic acids and diamine, polyamides, oligomers and copolymers of alpha amino acids such as glycine, lysine, aspartic acid, cysteine, ornithine and the like. Polyolefins include polyacylamide, polyacrylic acid, polymaleic acid, poly(hydroxyethylacrylic ester) and the like. These polypeptides and polyolefins will be tagged with such groups as fluorescein, rhodamine, a diazo dye, colloidal gold, luciferin, radioactive iodine and the like.

For the preparation of the visualization polymer, preferred coupling agent-chemical group bonding arrangements include:

1. A diacyl or di(iminoester) derivative of an aliphatic dicarboxylic acid of from 4 to 20 carbons which will form amide or amidine bonds with epsilon or primary amine groups of monomers functioning as units of the polymer.

2. A reactive diacyl or dihydrazide derivative of an aliphatic dicarboxylic acid of from 4 to 20 carbons or an aliphatic dihydrazine of from 4 to 20 carbons which will form amide or hydrazone groups with 1,2-diol groups of monomers functioning as units of the polymer when the 1,2-diol is oxidized to a dialdehyde, or which will form amide groups with carboxylic acid groups of monomers functioning as units of the polymer.

3. A reactive olefin derivative of an N-alkyl bis(maleimide) of from 4 to 20 carbons in the alkyl group which will form disulfide groups with mercaptan groups present in monomers functioning as units of the polymer.

4. A reactive aliphatic heterobifunctional reagent substituted with an N-maleimide group and either an iminoester or an N-(carbonyloxy)imide group wherein the aliphatic chain length is from 4 to 20 carbons, which will form a suifide group with a mercaptan group of a monomer functioning as a unit of the polymer and will form an amidine or amide group with an amine group an adjacent monomer functioning as a unit of the polymer.

5. A reactive aliphatic heterobifunctional reagent substituted with Schiff base protected amine group and an acyl or iminoester derivative group of a carboxylic acid wherein the aliphatic chain length is from 4 to 20 carbons, which will form an amide or amidine bond with an amine group of a monomer functioning as a unit of the polymer, and after removal of the Schiff base protecting group, will form an amide bond by carbonyl dimidazole or diimide coupling with a carboxyl group of an adjacent monomer functioning as a unit of the polymer.

6. A trifunctional lysyl lysine reagent which will form imine or amide bonds with oxidized 1,2-diol groups or carboxylic acid groups respectively which are present in monomers functioning as units of polymer.

The invention is as well directed to a detection kit for analysis of the presence of a target molecule especially in a biological material. The kit includes metered quantities of a mixture of a detection-visualization complex or the components thereof as set forth above, which is specific for the target molecule, and a standardized quantity of the same visualization polymer. The kit may be in the form of a colorimetric, fluorescent, luminescent or radioactive indicator in which the test quantities and standards are in aqueous solution and in appropriate containers for colorimetric, fluorescent, luminescent or radioactive analysis. The kit may also be in the form of test papers and standard papers such as nitrocellulose which will permit visualization of the target molecules.

BRIEF DESCRIPTION OF THE FIGURES

The Figures illustrate the results of detection tests conducted according to the invention.

DETAILED DESCRIPTION OF THE INVENTION

Figure 1:
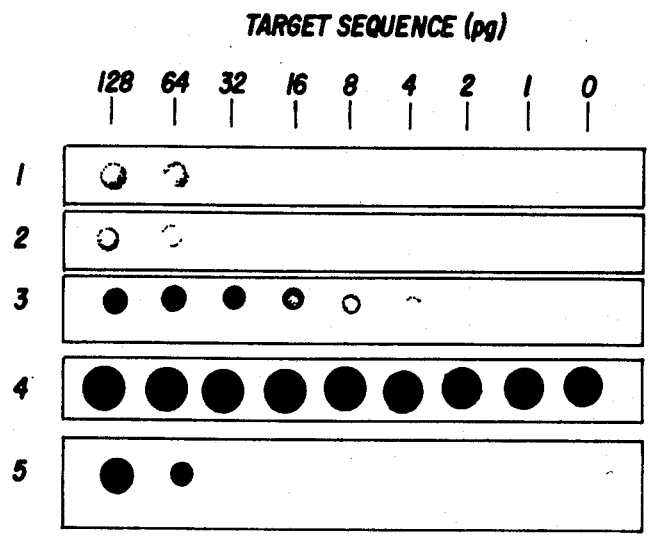
FIG. 1 shows detection of Biotin labelled DNA on nitrocellulose dot blots using a polyenzyme/avidin complex.

The visualization polymers and complexes of the present invention detect and chemically amplify the presence of minute quantities of inorganic or organic target molecules which may be found in biological material. Generally, the detection is based upon interaction between the polymer, its complex and the target molecule to be detected. The polymer is carried in a complex carrying arrangement which can bind with specific target molecules and exclude others. Quantitative determination of the target is made by measuring the amount of polymer present in the association formed between the target molecule and carrying arrangement. Signal amplification is provided by the multiple units in the polymer in each association.

The units of the polymer are an important feature providing visualization of the target carrying arrangement association. The units can contain visualization tags or can react with a substrate which can be utilized as a means for quantitative measurement. This measurement may be accomplished by production of a readily identifiable substrate product or production of a spectroscopic signal, as well as other, similar types of nondestructive quantitative analytic methods for measurement. Preferably, the visualization will be based upon the production of color, fluorescence, luminescence, radioactivity, high electron density as well as other forms of spectroscopic measurements.

When the units are enzymes they can generate products which are capable of producing such spectroscopic measurement. For example, they may catalyze reaction of substrates to produce colored, fluorescent, luminescent, electron dense or radioactive products.

Alternatively, the tagged units may be directly utilized as tools for spectroscopic measurement. For example, the natural or synthetic polypeptides, polyols, polyolefins or carbohydrates may be tagged with chemical groups which have coloration, fluorescent, luminescent, electron dense or radioactive properties. These may then be used for spectroscopic measurement.

Enzymes and tagged polypeptides, polyols, polyolefins or carbohydrates possessing the foregoing properties are well-known as means for spectroscopic quantification. When placed in an an appropriate spectrometer, the enzymatic substrate or tag will cause a spectrographic change which will indicate the quantity of target present. This process is commonly referred to as visualization and the spectral change is termed the signal produced by the visualization group (the substrate or tag).

The quantity of target to be detected usually will be minute and if the signal from the complex-target association were produced on an equivalent basis, it also would be extremely weak. However, the carrying arrangement and its visualization polymers chemically amplify the signal so that minute quantities of target will produce a strong, readily determined signal. Amplification is achieved by the polymer because it comprises multiple visualization units. The signal provided by each unit is maintained by the polymer. Consequently, its signal is the sum of the signals of its units. In addition, the carrying arrangement may contain multiple numbers of polymer. Although it is not necessary, this multiple arrangement is preferred since it provides further amplification.

The visualization polymer of the invention comprises multiple visualization units monomer directly bonded together or indirectly linked together by a coupling agent bonded to chemical groups or backbone moieties of the units. Each unit also possesses a site or sites which provide the visualization signal. That is it may be a site for enzymatic action or a site to which a visualization tag or tags are attached. The visualization signal activity of the polymer depends upon production of a signal by each unit. Accordingly, the visualization site or sites should be substantially preserved in its or their original form so that the site activity is not substantially decreased. It follows that chemical modification of the units should be conducted in a manner which does not substantially affect the site or sites.

To this end, the direct bonding or coupling agent linkage should join chemical groups or backbone moieties of the units which are at least one atom and preferably at least 3 to 5 atoms away from the visualization site or sites. Also, the choice of chemical groups or backbone moieties for direct bonding or linking with coupling agent should be limited to those which are not present within the site or which are not necessary for site conformation and three dimensional configuration. This choice will be more important for enzyme proteins than for tagged natural or synthetic polypeptides polyols, polyolefins or carbohydrates; however, interference with the production of tag fluorescence, luminescence, coloration, radioactivity or high electron density should also be avoided.

Generally, these site preservation requirements may be met in several ways. If the types of biochemical substructures or chemical residues making up the monomer structure are known, then one which is not part of the visualization site may be chosen as the structure containing the reactive chemical groups or backbone moieties for coupling. Usually, however, a semi-emperic method will be used for choice of the appropriate reactive chemical groups or backbone moieties.

According to the substructure/residue method, the chemical construction of the units will be investigated. The unit backbone substituted groups and functional structures such as sugar groups, lipids, oligomer side chains and the like which are not necessary for visualization site action will be identified. Typically, this would be determined by removal modification or modification of such substructures and study of the activity of the resulting product. Chemical groups or backbone moieties present primarily within these substructures may then be used for direct bonding or indirect linking with the coupling agent. For example, the sugar groups of a glycoprotein which are not necessary for enzymatic activity can be oxidized to dialdehyde groups and reacted with a hydrazine coupling agent to form the visualization polymer.

If the chemical sequence of the unit, such as the amino acid sequence of a protein, can be determined, this may also be utilized to guide direct bonding or indirect linking. Analysis of the sequence for the active site as well as the three dimensional configuration will show which unit structural subunits are not essential to functioning of the site and/or not present within it. The reactive chemical groups or backbone moieties of these subunits may be used for bonding or linking with the coupling agent. For example, if the unit is a protein and it is found to contain a dipeptide side chain ending with cysteine, the mercaptan group of the cysteine may be cross-linked to cysteine of another similar protein by reaction with bis (N-butylenylmaleimide).

According to the semi-emperic method, the reactive chemical groups and backbone moieties of the unit can be determined by appropriate spectrographic and chemical analysis. These include techniques such as NMR, IR, chemical derivatization, electrophoresis, osmometry, amino acid analysis, elemental analysis, mass spectrometry and the like. The groups and moieties identified may include amine groups, mercaptan groups, carboxyl groups, hydroxyl groups, sugar groups, carbohydrate groups, ester groups, lipid groups, and amide bonds, labile carbon-carbon bonds and carbon-hydrogen bonds the like. Other measurements such as the relation of derivatization and site activity, relation of pH and site activity and type of site reaction produced in the case of an enzyme will help determine a priority for the functional groups based upon the probability of their presence within the vicinity of the active site. A typical priority will be 1. an epsilon or primary amine group, 2. sugar group, 3. carboxyl group, 4. mercaptan group, 5. hydroxyl group, 6.

lipid group. If derivatization of amine groups such as those of lysine residues produces a derivatized product devoid of site activity, then the foregoing priority will change and the amine group will be last.

Under usual emperic procedures, several versions of polymer will be prepared using a selection of several of the reactive chemical groups or backbone moieties. The activities of the several versions are then tested and the one selected of which has the highest activity. Typically, the selection of chemical groups or backbone moieties will encompass three or four types which are least likely to affect the activity of the visualization site. Each type of reactive chemical group or backbone moiety may eventually be tried if results with the first few are unsatisfactory. Emperic examination of each version of polymer will allow identification of the one with the highest activity.

The units having visualization sites which are very sensitive to the chemical group/backbone moiety bonding arrangement are enzymes. The catalytic site typically will have a conformation closely fitting the substrate and chemical modification which disturbs the three dimensional configuration of the catalytic site may adversely affect the activity of the polymer. Following the foregoing procedures, enzyme site activity can be preserved. Furthermore, the enzyme catalytic site may be protected during bonding or linking by reversably binding it with substrate.

Tagged natural or synthetic polypeptide, polyol, polyolefin or carbohydrate will have visualization sites which are substantially less sensitive to the chemical group/backbone moiety bonding arrangement. The fluorescent group, dye, luminescent group, radioactive group or electron dense group which acts as the tag typically will not be subject to variations in activity when adjacent chemical groups or backbone moieties are directly bonded or indirectly linked with coupling agent. Care must be taken, however, to assure that the direct bonding or coupling agent does not also react or otherwise interfere with the tag to lessen its visualization activity. Moreover, if the tag is to be converted to an active group after the visualization polymer-target association is made, then the position of the chemical group or backbone moiety linkage should not interfere with the conversion.

Generally, the chemical groups and backbone moieties should be at least one atom away from the visualization site. Enzyme protein monomers will be bonded or linked preferably about 3 to 5 atoms away from the visualization site.

The visualization polymer structure is multiple visualization units either directly interbonded or cross-linked by coupling agent. The structural and functional character of the polymer will be similar to that of the monomer units. The number of units per polymer will depend upon the extent of coupling, the stability of the resulting polymer, the reactivity of the chemical groups or backbone moieties relative to the polymer chain length and the position of the groups or moieties along the unit backbone.

Generally, the number of units incorporated into the polymer may vary from as few as two to three to as many as thirty to one hundred per polymer. Higher multiples are also possible provided that the polymer chain length is not of an order which will render the polymer extremely insoluble in aqueous solution or will be extremely suseptible toward mechanical cleavage.

The polymer may be linear or it may be branched There may be single or multiple coupling between two adacent units. Coupling may occur at any point along the unit chain so that adjacent units may lie end to end, or may partially or fully overlap. As a result, the three dimensional structure of the polymer may have all of these features. It may be linear but more typically will be a combination of linear and branching units. Partial overlap will typically occur and multiple coupling will also be present.

The accessibility of the chemical groups or backbone moieties will also, affect polymer length. If they are buried within the unit structure, steric inhibition will tend to hinder coupling of a high number of units. This effect may be compensated by use of coupling agents having a chain length greater than about ten carbons in length. In a more usual arrangement, the reactive chemical groups or backbone moieties will be readily accessible and will lie either within the proximate ends of the unit chain or will lie within an accessible side chain or group which extends away from the inner region of the three dimensional structure of the unit. This type of group or moiety will be amenable toward coupling of high multiples of units. Typically, direct bonding or any chain length of coupling agent may be employed. However, coupling readily accessible groups or moieties with agents which will hold apart the units of the polymer will sometimes provide advantage. This will allow facile approach of substrate or reactant and will prevent adverse interaction among the units of the polymer. Typically, agents having a carbon chain length of from about 4 to about 20 carbons will be preferred.

The coupling agent linking units together generally is derived from a bifunctional or multifunctional organic cross-linking reagent of foregoing formula I. In this context, the term coupling agent will indicate the group in its coupled form with a chemical group or backbone moiety. The term cross-linking reagent will indicate the chemical form of the agent before it is reacted with a chemical group or backbone moiety.

Choice of the coupling agent/cross-linking reagent will depend upon the choice of the reactive chemical group or backbone moiety to be coupled and the agent chain length which will avoid intraunit interference within the polymer. Scheme I illustrates the general plan for reagent and chemical group or backbone moiety reaction.

In each of reactions 1-6 of Scheme 1, the bi or multifunctional cross-linking reagent of formula I is used. The generic formula for this reagent is 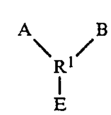 wherein A, B and E are reactive groups as specified above and $R^1$ is as specified above. In the reactions, a specific reactive group for A and its reaction with a unit chemical group or backbone moiety are given. Groups B and E, which are not designated, may be the same, may be chosen from any of the other reactive groups, or one of B and E may be hydrogen. In this manner, the reactions illustrate cross linking reactions with homo- (bi or multi) functional reagents wherein the reactive groups are the same and with hetero- (bi or multi) functional reagents wherein the reactive groups are different.

$R^1$ of formula I usually will be substantially linear and will have little, if any, branching. Preferably, $R^1$ is an alkylenyl group of the formula $-(CH_2)_j-$; a cycloalkylenyl group of the formula $-CH[(CH_2)_k]_2CH-$; or an aryl group of the formula $-(CH_2-C_6H_4-(CH_2)_m-$ wherein j is an integer of from about 2 to about 30, k is an integer from about 0 to 6 and the sum of k's will be 4,5,6,7 or 8, and 1 and m are integers independently selected from 0 to about 20. Especially preferred $R^1$ groups will include alkylenyl having j from 3 to 14 and aryl having 1 and m from 0 to 5 and having a para substitution. Preferred embodiments include propylenyl, butylenyl, hexylenyl, nonylenyl undecylenyl, dodecylenyl cyclohexylenyl, phenylenyl or xylenyl.

Reactions 1A, 1B, and 1C of Scheme I show the coupling of a free amine chemical group. Usually, this will be an epsilon or primary amine group of an alpha amino acid residue of the protein unit. Examples of amino acids containing an epsilon amino groups include lysine, and arginine. Examples of amino acids with primary amine groups include the twenty alpha amino acids typically found in protein. Amine groups on other kinds of unit such as amino sugars or aminonucleotides can also be coupled with this reaction.

The reagents of formula I1A, which are used to perform reaction 1A, include those known carboxylic acid derivatives which will react with amines to produce amides. Included are acyl halides, mixed anhydrides, activated esters, acyl imidazoles derived from carbonyldimidazole, N-oxasuccinimides produced by the dehydration reaction of the corresponding carboxylic acid and an N-hydroxysuccinimide with a diimide dehydration reagent, amide formation with dehydrating reagents such as diimides, phosphorus pentoxide in organic solvent, and phosphorus oxychloride. These groups are indicated as X in reaction 1A.

Generally, these acid derivatives may be prepared by condensation of the corresponding carboxylic acid and X group reagent. They may be reacted with the amine chemical group according to reaction 1A, using aqueous or polar organic solvent under mild conditions. The methods and use of these reagents are known; see for example "Reagents For Organic Synthesis", L. Fiezer, M. Fiezer, Vol. 1-8, Wiley & Son; "Cross Linking Reagents" (1980 Ed.), Pierce Biochemical Reagent Catalog, Pierce Chemical Co., Rockford Ill. and references therein, or "Advanced Organic Chemistry" J. March, McGraw Hill (1968).

Reaction 1B shows coupling of an iminoester salt reagent of formula I1B with an amine chemical group to produce an amidine coupling agent linkage. This method is also known in the art. The reagent may be generated from the acidic alcoholysis of the corresponding nitrile. The amidine formation reaction may be conducted in aqueous or polar organic solvent under mild conditions. The methods and procedures are known; see for example Lockhart, et. al., Can. J. Biochem., 53, 861–867 (1975) and Pierce Biochemical Reagent Catalog and references therein, supra.

Reaction 1C shows condensation of an amine chemical group with an aldehyde reagent of formula I1C to form a bis Schiff base (imine). Examples include glutaraldehyde and other tissue fixing reagents. Conditions include use of polar organic solvent and mild temperatures. These methods are known in the art.

Reactions 2A, 2B and 2C of Scheme I show the condensation coupling of an aldehyde chemical group with amines and amine derivative reagents to form imine and imine derivative compounds. These reagents and reactions include primary amine reagents of formula I2A which react to form a Schiff base (imine), see reaction 2A; substituted hydrazine reagents of formula I2B which react to form substituted hydrazones, see reaction 2B; and acyl hydrazide reagents of formula I2C which react to form acyl hydrazones, see reaction 2C. The aldehyde functional moiety will be generated, in turn, by oxidative cleavage of any 1,2-diol (glycol) group within the unit except that oxidative cleavage of glycol groups which would result in cleavage of the unit chain cannot be used. Usually, the glycol group will be found on a side chain attached to the unit backbone. Examples include carbohydrate and starch groups as well as dihydroxy alkyl, cycloalkyl and acylalkyl groups.

Conditions for reaction 2A, 2B and 2C include use of aqueous or polar organic solvents and mild to moderate temperatures. These methods and procedures are well known in the art, see for example "Basic Principles Of Organic Chemistry", Roberts and Caserio, W. A. Benjamin (1965) or "Qualitative Organic Analysis," Shriner and Fuson, Wiley Interscience (1966).

Reactions 3A and 3B of Scheme I show the coupling of a mercapto chemical group with cross-linking reagent I3A and I3B to form the polymer linked by sulfide groups. Reaction 3A is condensation of the mercaptan chemical group with alpha halomethylcarbonyl reagent I3A wherein Y is a halogen to form carbonyl methylene sulfide P3A; see, for example, Hixon, et. al., Biochemistry, 14, 425 (1975). Reaction 3B is coupling of the mercaptan chemical group with maleimide reagent I3B to form succinyl 3-sulfide P3P.

The mercaptan groups will be found within the unit as part of a cysteine, glutathione, cystine or similar amino acid unit. They may also be present as a derivative of a sugar or lipid group.

Conditions for reaction 3A will include aqueous or polar organic solvent, an acid scavenger such as pyridine and mild to moderate temperatures. Conditions for reaction 3B will include aqueous or polar organic solvent, optional mild acid catalyst and mild to moderate temperatures. These methods and procedures are known in the art, see Pierce Biochemical catalog and references therein supra.

Reactions 4A and B show the condensation coupling of a carboxylic acid chemical group and an amine or acylhydrazide reagent. Reagent I4A may be coupled with the carboxylic acid group directly through the use of compounds such as diimide or carbonyl diimidazole, see the foregoing description for reaction 1A. It may also be coupled by forming a carboxylic acid derivative such as the mixed anhydride, an activated ester or an acyl halide. Reagent I4B may be coupled with the carboxylic acid group through use of a dehydrating reagent such as a carbodiimide; see reaction 1A. Carboxylic acid containing substituents of units would provide the carboxylic acid group directly or may be oxidized to provide it. These include amino acid residues such as aspartic acid, glutamic acid as well as oxidized forms of sugar side chains. Lipids, carbohydrates and olefinic carboxylic acids are also included. These methods are known in the art, see for example "Organic Syntheses", Wiley, New York, Coll. Vol 1-V.

Reaction 5 shows esterification of an hydroxy function moiety with an activated carboxylic acid reagent I5. These would include the same reagents as given for formula I1A. In this synthetic method, if there are free, reactive amine groups of the unit, they could first be protected with a removable protecting group such as a Schiff base, i.e., condensation of the amine groups with an aromatic aldehyde such as p-methoxybenzaldehyde or benzaldehyde which can be removed with dilute hydrogen chloride in acetone. Other known amine protecting groups may also be used. These include dinitrofluorobenzene, t-butoxy groups and organosilanes.

After protection, esterfication is conducted using the activated acid reagent. Unit residues which will esterify in this fashion will include amino acid residues of serine, threonine, hydroxylysine, tyrosine, thyroxine, hydroxyproline, and the like. Other residues include carbohydrate, starch, lipid and olefinic residues with hydroxyl substitutions. These include hexoses, pentoses, dextrans, amyloses, glycerols, fatty acid derivatives, methylhydroxymethacrylate, hydroxymethyl acrylate and similar compounds.

Conditions for the esterification include aqueous or polar organic solvent, and mild to moderate temperatures. These methods and procedures are known in the art; see, for example, the foregoing treatises on organic synthesis.

Reaction 6 shows insertion of a nitrene from azide reagent I6 into a carbon hydrogen bond. This reaction is nonspecific and can take place at any point within the unit. Since the nitrene is short lived, readily accessible carbon hydrogen bonds will be attacked first. This reaction is especially useful for coupling of the tagged natural or synthetic polypeptides polyols, polyolefins and carbohydrates as well as for enzymes having C—H bonds which are readily accessible and not involved with site activity.

The conditions for reaction include polar organic solvent and irradiation with 300-400 nm light. The methods and procedures for this reaction are known, see for example Bisson, *J. Biol. Chem.*, 253 1874–1880 (1978) or Pierce Biochemical Catalog and references therein, supra.

Reaction 7 is the direct bonding polymerization of the monomer units. It may be accomplished by enzymtic oxidative cross-linking, photolytic free radical generation and cross-linking or free radical initiation with such reagents as persulfite, hydrogen peroxide and triplet oxygen.

Table 1 lists the types of groups which may function as X, Y, and X' in formulas I1A, I3A and I5 of Scheme 1. These have been described in conjunction with the explanation of each reaction.

Scheme I
Bonding Or Linking Reaction:

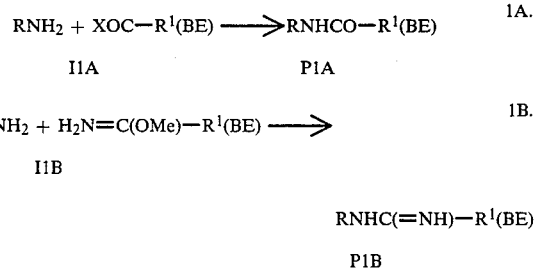

-continued
Scheme I
Bonding Or Linking Reaction:

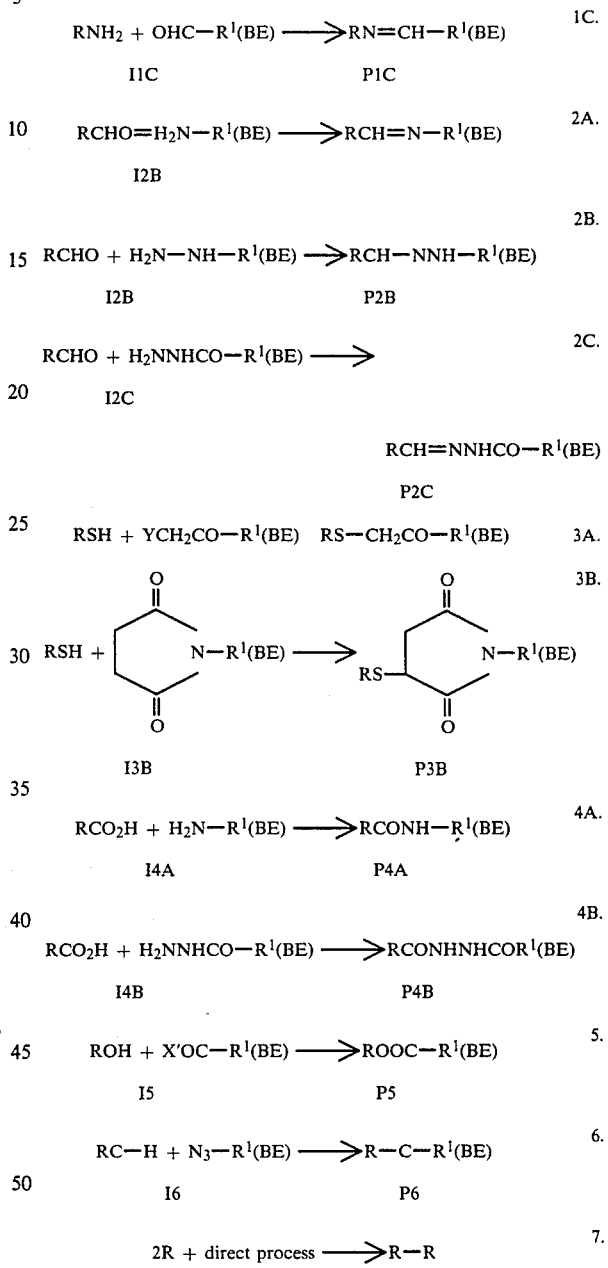

Scheme I Notes

R is a visualization unit. The bi or multifunctional cross-linking reagent of formula I is designated in each of the reactions. One of the reactive groups (A) of formula I has been specified for each reaction. The other reactive groups (B, E) of formula I may be chosen from any of the designations indicated for A of reactions 1-7 or one of (B, E) may be hydrogen. Homo and hetero bi-functional and multifunctional reagents are included. R1 of formula I and formula P of each of the reactions is an aliphatic group of at least 2 carbons or an aromatic group. Preferably, $R^1$ is an alkylenyl group, $-(CH_2)_j-$; or an acyl group, $-(CH_2)_k-C_6H_4-(CH_2)_l-$ wherein j is about 2 to about 30, and k and l independently are 0 to about 20.

TABLE 1

1. X groups include:
    halide, especially Cl, Br, I
    2,4-dinitrophenoxy (an activated ester)
    p toluene sulfonyloxy
    pivaloyloxy
    t-butoxycarbonyloxy
    acetoxy.
2. Y groups include:
    Cl, Br, I.
3. X' groups include:
    halide, expecially Cl, Br, I
    2,4-dinitrophenoxy (an activated ester)
    pivaloyloxy
    t-butoxycarbonyloxy
    acetoxy.

The units may be any enzyme which will react with an appropriate substrate to produce a colored, fluorescent, luminescent, electron dense or radioactive product. Also, the enzyme may react with a colored, fluorescent or luminescent substrate and quench it. The production or quenching of color, fluorescence or luminescence may result from direct enzyme catalysis or the enzyme may produce an intermediate which enters into a chain of reactions to produce or quench color fluorescence or luminescence.

If an electron dense or radioactive substrate is to be used, the enzyme will act to immobilize it. This may be accomplished by rendering the substrate insoluble, chemically reactive toward the enzyme or otherwise generating an immobilizing physical characteristic. With this type of visualization polymer, the quantity of radioactivity immobilized by the enzymatic reaction or an electron microscopy determination of the quantity of electron dense material present will allow analysis of the minute quantity of target. Examples of such enzymes include peroxidase, alkaline or acidic phosphatase, galactosidase, glucose oxidase, NADPase, luciferase, carboxypeptidase and the like.

The units may also be natural or synthetic polypeptides, polyols, polyolefins or carbohydrates which are tagged. These may be based upon a polyamide backbone, a polyether backbone, a polyvinyl backbone, or poly (sugar) backbone. For the polyamide, the amino acid or diamine compound and dicarboxylic acid compound used to make the backbone may be nonfunctional, i.e., composed of a methylene unit chain ending in the appropriate functional groups, or it may be substituted with groups which would provide side chain functionality. Examples would include glycine, alanine, serine, lysine, aspartic acid and the like as amino acids. Examples of diacids and diamines include arylene or alkylene dicarboxylic acid having at least 6 carbons in the arylene group or 1 to 20 carbons in the alkylene group, and arylene or alkylene diamines having at least 6 carbons in the arylene group and 1 to 20 carbons in the alkylene group. Examples will include poly(3-aminopropionic acid), polyglycine poly(glycyl-lysine), poly(N-(aminohexyl)alipic amide), poly(N-(aminobutyl)-terephthalamide) and the like.

For the polyethers, epoxides and/or oxacyclic compounds with or without hydroxyl substitution can be used as backbone building blocks. Acidic condensation will couple the oxide compounds. Also, the polyols may have a poly(vinyl) backbone with hydroxylic substitution. These may be formed by vinyl/free radical polymerization of alkyl alcohol, butene diol and the like.

For the polyvinyls, vinyl compounds with or without chemical group substitution may be used as backbone building blocks. Vinyl/free radical polymerization of such compounds as acrylamide, acrylic acid, maleic acid, alkyl sulfide, acrylonitrile, methyl acrylate, hydroxyethyl acrylate, alkenyl amine, acrolein, etc. will produce the polyolefin monomers.

For the poly(sugar), glycosidic linking through hemiketal condensation of simple sugar building blocks can be used as the carbohydrate backbone formation process. Carbohydrates such as methoxy cellulose, poly(glucose) starch, dextran, polymaltose, amylose, etc. are examples.

The chemical tags include the known, colored, fluorescent, luminescent, radioactive and electron dense probes which will chemically bond with substituents present in a natural or synthetic polypeptides polyols, polyolefins and carbohydrates. These include probes with carboxylic acid derivative substituents, sulfonic acid substituents, imino ester substituents, maleimide substituents, aldehyde substituents, azide substituents and amine substituents which will react with the appropriate functional group of the unit as outlined in Scheme I and Table 1. The probes will be monofunctional rather than difunctional so that they may react only once with a unit chemical group or backbone moiety. Examples of color tags include azido indigo dye, and congo red with sulfonyl chloride substitution. Examples of fluorescent tags include fluorescein with an azido or sulfonyl chloride reactive substituent, 3-azido-(2,7)-naphthalene disulfonate and rhodamine. Examples of radioactive tags include wood reagent (methyl p-hydroxybenzimidate) HCl which can be iodinated, and p-iodobenzenesulfonyl chloride. Examples of electron dense tags include collodial gold, colloidal silver, ferritin, metal binding proteins and reactive lead salts.

Isolation and purification of the visualization polymer of the invention may be accomplished by known techniques used for polymer isolations. These include dialyzation, lyophilization, chromatography, electrophoresis, centrifugation, precipitation by electrolyte adjustment or solvent lipophilicity and the like.

The carrying arrangement of visualization polymer and detecting agent may be direct or indirect. The direct carrying arrangement will have the detecting agent covalently bonded to the visualization polymer by a bifunctional or multifunctional cross-linking reagent. Generally, the bonding will follow Scheme I and method given for linking the visualization units of the polymer. These methods are generally known; for example see K. Peters, et. al., *Ann Rev. Biochem.*, 46, 523–551 (1977); F. Wold, "Methods In Enzymology XXV", pp 623–651 (1972) or M. Das, et al., *Ann Rev. Biophys.* Bioeng., 8 165–193 (1979). As with the visualization polymer, covalent linkage with chemical groups or backbone moieties of the detecting agent should take place in a region of the agent which will not interfere with its ability to detect the target. This may be determined by any of the methods given above, especially the emperic method.

The indirect carrying arrangement may be of two types. In the first, the detecting agent may be multivalent and have an affinity for the visualization polymer as well as the target. For example, it may be accomplished by employing a multivalent antibody which cross-reacts with the units of the visualization polymer and by utilizing the appropriate amount of antibody and polymer so that at least one of the affinity sites of the antibody remains open. The visualization polymer may also be bonded to a ligand which complexes with a multivalent detecting agent. This will accomplish the same kind of carrying arrangement.

In the second type of indirect carrying arrangement, there will be an intermediate ligand binding compound interspersed between the detecting agent and the visualization polymer. It will display a high affinity for specific ligands and will include an antibody, lectin, avidin, streptavidin, a DNA repressor protein, a high affinity enzyme, a sequence specific polynucleotide binding protein or a complementary polynucleotide sequence. The agent and polymer will be correspondingly labelled with the appropriate ligand. The ligand may be joined to the detecting agent and polymer through a linker similar to a bi or multifunctional cross-linking reagent $R^1(ABE)$ of Scheme I. Attachment of the linker to the agent and polymer will follow the methods given for the reagent coupling according to Scheme I. Also, the ligand may be substituted for a reactive group of the bi or multifunctional cross-linking reagent $R^1(ABE)$ of scheme I.

Alternatively, the ligand may be covalently bonded directly to the detecting agent and polymer. That is, the ligand may be bonded to a chemical group of the polymer and detecting agent which may include an amine group, mercaptan group, carboxylic acid group, hydroxy group, aldehyde group or a C—H group. The procedures and reagents given according to Scheme I will be used for this purpose and the appropriate reaction will be chosen depending upon the kind of reactive group present on the ligand.

Methods for the preparation of the carrying arrangements and complexes of the invention follow the well known procedures given in the foregoing background. Examples include use of ligands such as biotin, iminobiotin, polynucleotide sequences, enzyme substrates, sugars, haptenes such as 2,4-dinitrophenol, 2,4-dinitrophenylalkylcarboxylic acid having from 1 to 20 carbons in the alkyl group, and carboxylic acid derivatives thereof. Other examples of haptenes include 2,4-dinitrophenylalkylamine having from 1 to 20 carbons in the alkyl, phenylarsenate, inistol and trinetrobenzene.

A preferred example of this type of carrying arrangement and complex is based upon use of a complementary strand of polynucleotide as a detecting agent for a specific native polynucleotide sequence. Avidin or streptavidin is used as the ligand binding compound and a functionalized biotin or imino biotin derivative is used as the ligand. Bonding the biotin or imino biotin to the visualization polymer and polynucleotide detecting agent may be accomplished directly or through use of a linker group. These methods are known in the art; see Langer et al., *Proc. Nat'l. Acad. Sci. U.S.A.*, 78, 6633-7 (1981); and follow the methods given for Scheme I except that one end of the bifunctional cross-linking reagent will have been reacted with biotin or iminobiotin. Accordingly, the complex includes avidin or streptavidin-(biotin or iminobiotin ligand)- visualization polymer. The carrying arrangement in addition includes the biotin or imino biotin labelled polynucleotide detecting agent.

The method of the invention utilizing this example can be practiced as follows. An isolated double strand of native polynucleotide to be detected, such as viral DNA, is broken or nicked with a DNAase at random points along each strand. Labelled nucleotide monomers are then translated into the nicks using a polymerase enzyme and the other associated strand as a template. Alternatively, the complementary strands can be directly labelled with biotin label. The labelled complementary pair of polynucleotide strands are then denatured and mixed with a denatured mixture of unknown native polynucleotides, suspected as containing the polynucleotide to be detected. If it is present, hybridization will occur and the labelled double strand may be visualized with the polymer complex.

A second preferred example of a complex is derived from the methods given in the Background for PAP or ABC complex methods or according to Langer et al., supra. In this example, avidin or streptavidin is used as the intermediate ligand, an antibody, lectin, or a sequence specific polynucleotide binding protein is used as the detecting agent and a biotin or imino biotin compound is used as the ligand complexing the visualization polymer and detecting agent with avidin or streptavidin.

In either of these two preferred examples, the biotin or imino biotin compound may be directly coupled with amine or hydroxy groups of the polymer and agent through the use of amide bond or ester bond forming coupling reagents respectively. These methods follow reactions 1 and 5 of Scheme I. It may also be coupled through a linker group such as that described above. The linker group is similar to the bifunctional cross-linking reagent ($R^1ABE$) of Scheme I except that one of the two reactive groups will be an amine or acylhydrazide group which is coupled with biotin or iminobiotin.

The visualization polymer of the present invention may be used to detect minute quantities of target molecules. These molecules may be found in biological material such as tissue and fluid as well as in artificial or synthetic systems. Examples include blood, lymph, urine, feces, organ tissue such as lung, liver, skin, kidney and the like, microorganisms, plant tissue, cultured cells, hybrid cells, cells with recombinant DNA, synthetic mixtures of polypeptides, immobilized enzyme systems, synthesized DNA and other biological material.

The target molecules may constitute any inorganic or organic species which is capable of producing an affinity with a detecting agent. Preferred targets will be found in the foregoing biological material and systems. Examples include proteins, lipids, carbohydrates, phospholipids, fats, nucleotides, nucleosides, nucleoside bases, polynucleotides, polypeptides, cancerogenic agents, drugs, antibiotics, pharmaceutical agents, controlled substances, polymers, silicones, organometallic compounds, heavy metals, metal-protein complexes, toxic inorganic salts, and other agents or compounds produced by or having an effect upon a biological organism or material derived therefrom.

Generally, the procedures for combination and, incubation of the detecting agents and targets are well known. They follow methods used for affinity and immumodiagnostics assays; see for example L. A. Sternbeyer, "Immunohistochemistry" cited above. For example, combination of metered amounts of agent and target in buffered aqueous solution followed by incubation at temperatures from ambient to about 37° C. for periods such as 5 minutes to 18 hr. will cause conjugation. Addition of the visualization polymer or its complex under similar conditions will then provide visualization. Finally, if the agent is bonded to the visualization polymer, similar techniques can be followed.

Use of the visualization polymer for the foregoing detection purposes has advantage since it allows detection of extremely minute quantities of target molecules. It may be employed in medical diagnostic laboratory as an analytical technique for identification of biological products in fluids and tissues which are indicative of a disease state or malcondition. These would include for example, abnormal amounts of growth hormone, the presence of human gonadotropin indicating cancer, detection of viral invasion, quantification of hormone and regulatory enzyme levels. Also, it may be employed to perform normal fluid and tissue chemistry analyses and may be employed in the biochemical research laboratory as a tool for identification of biochemical substances.

The visualization polymer may be used in synthetic protein or polynucleotide work to identify synthesized, semisynthetic or native proteins and synthesized, recombinant or native polynucleotides. Applications will be found in the course of preparative or bulk work to produce useful proteins such as insulin, interferon, ACTH, gonadotropin, oxytocin, pituitary hormone, LH, FSH and the like by such techniques as recombinant DNA or hybridomas.

The carrying arrangement of detecting agent and visualization polymer complex will be the form for use to perform the foregoing analyses. Since the polymer will provide multiple signals from the carrying arrangement association with the target, chemical amplification will result. In the preferred form of the carrying arrangement wherein a complex of polymer and ligand binding compound is employed, the signal amplification by the polymer will be further increased by multivalent liganding of multiple numbers of polymer to each molecule of detecting agent. Accordingly, in the preferred embodiments employing an antibody or complementary polynucleotide sequence detecting agent, biotin or immobiotin labels, on the agent and polymer, and an avidin or streptavidin, detection of femtomole ($10^{-15}$) quantitites can be achieved. This will also depend in part upon employing a sensitive visualization unit system and the appropriate carbon chain linker lengths for both the biotin labels and the coupling agent of the polymer. An example would be use of the enzymes alkaline phosphatase or horseradish peroxidase coupled as visualization polymer by epsilon amino group bonding with an active diacyl derivative of suberic acid, and use of biotin labels with carbon chain linkers of from 6 to 14 carbon in length.

The polymer, complex and carrying arrangement of the invention may be formulated as an integral part of a solid or liquid detection system and kit. Colorimetric, fluorescent, luminescent and radioactive systems may be prepared in this manner. Such systems and kits would include the detecting components, i.e., the polymer, its complex with a ligand, a ligand binding compound, and the detecting agent as well as the appropriate chemicals, reagents and solutions in metered amounts and standardized concentrations also. For example, if enzymatic action with a substrate to produce a colored product is to be the visualization procedure employing the polymer, the system and kit will contain the chemicals, substrate and reagents necessary for performing this analysis. These materials will be present as metered quantities so that the light absorption produced by the colored product may be used in conjunction with a standard Beer's Law mathematical formula to determine the concentration of target detected. Usually, a standard reaction of polymer with substrate will be employed as a control and reference, although standard graphs of absorption relative to concentration may also be utilized.

Fluorimetric, lumimetric and radiometric analyses may be performed in a similar fashion. The intensity of fluorescence, luminescence or radioactivity produced by the polymer in the carrying arrangement associated with the target will be measured by the appropriate electronic machine. Necessary reagents and chemicals will also be present. Metered amounts of components will be employed so that the intensity value may be correlated with the quantity of target using a standard Beer's Law mathematical formula.

In these systems, a concentration of detecting agent-visualization polymer complex will be used in the test solution which is sufficient to associate with all the target to be detected. Preferably, the concentration will provide an excess amount. The target may be grossly separated from other material by sedimentation, by centrifugation, or otherwise separated by such techniques as high pressure liquid chromatography, gel permeation chromatography, electrophoresis, precipitation, thin layer chromatography, paper chromatography or similar techniques. However, this is not necessary for the purposes of this invention. The signal producing reaction will be initiated by forming the target-detecting agent conjugate followed by forming the visualization polymer-detecting agent associative arrangement and measuring the visualization signal from this arrangement. Comparison of the signal intensity with a standard graph will yield the quantity of target. Other techniques such as conjugate-complex exchange, which are known in the field of immunoanalysis, may also be used.

With all of the foregoing liquid and solid analysis methods, qualitative detection may also be made. Since this object will be determination of the presence of the target to be detected rather than quantity, standardization need not be used. The qualitative techniques will generally follow the methods for the foregoing quantitative techniques.

The invention will now be further illustrated through the aid of examples. These examples are not limiting and other similar procedures as shown by the examples will be readily apparent to those skilled in the art. All measurements are provided in the metric system unless otherwise noted.

EXAMPLES

Abbreviations and acronyms used in the examples are defined as follows.

Bio-4-dUTP, Bio-11-dUTP and Bio-16-dUTP; analogs of TTP that contain a biotin molecule linked to the C-5 position of the pyrimidine ring through linker arms that are 4,11 and 16 atoms long, respectively.

Bio-4-DNA, Bio-11-DNA and Bio-16-DNA are DNA probes prepared with Bio-4, Bio-11 or Bio-16 dUTP analogs, respectively.

DNA is poly(deoxyribonucleic acid).

IgG is immunoglobulin G fraction.

DSS is disuccinimidyl suberate.

BACSE is biotinyl-epsilon-amino caproic acid N-hydroxysuccinimide ester.

NMZT buffer is defined at p 48.

poly ABAP Complex is avidin-biotinylated alkaline phosphatase polymer complex

DAB is 3,3-diaminobenzidene.

EAC is ethyl aminocarbazole.

The following examples show the synthesis of visualization polymers of intestinal alkaline phosphatase and the construction of avidin (or streptavidin) enzyme polymer complexes. These polymers provide visualization which is 20–50 fold more sensitive than heretofore known immunologic or affinity reagents. Also described are rapid and sensitive procedures for visualizing biotin-labeled DNA probes after hybridization to target sequences immobilized on nitrocellulose filters and methods for detecting protein antigens in tissue sections after application to glass slides.

The examples and procedures chosen illustrate application of the invention to detection of a genetic sequence associated with human placental DNA and a peptide hormone associated with malignancy. These are the alpha and beta globin genes in human placental DNA and human chorionic gonadotropin. Analysis of human genes can be used for prenatal diagnosis of genetic disorders and analysis of hCGT can be used as an oncofetal marker of cancer.

Affinity purified rabbit anti-biotin IgG was prepared as described Langer-Safer, *Proc. Natl. Acad. Sci. USA*, 79, 4381 (1982). An ammonium sulfate fraction of goat anti-biotin IgG was provided by Enzo Biochem Inc., NY. Biotinylated rabbit anti-goat IgG, biotinylated goat anti-rabbit IgG, and avidin DH - biotinylated horseradish peroxidase complex (Vectastain ABC kit) were purchased, or provided as gifts, from Vector Laboratories, Inc., Burlingame, CA. Streptavidin, Hoffman, *Proc. Natl. Acad. Sci. USA*, 77, 4666 (1980), was obtained from either Bethesda Research Laboratories, Inc., Gaithersberg, MD or Enzo Biochem Inc. Calf intestinal alkaline phosphatase (Cat. No. 567-752) and pancreatic DNAse type I were purchased from Boehringer Mannheim, Indianapolis, Ind. Biotinyl-epsilon-amino caproic acid N-hydroxysuccinimide ester was synthesized according to Costello et. al., *Clin. Chem.*, 25, 1572 (1879). Disuccinimidyl suberate was a product of Pierce Chemical Co., Rockford, Ill. Restriction endonucleases and E. coli DNA polymerase I were obtained from New England Biolabs, Inc., Beverly, MA. Agarose (type II), bovine serum albumin (BSA, fraction V), 5-bromo-4-chloro-3-indolyl phosphate p-toluidine salt, cadaverine free base, 3,3'-diaminobenzidine tetrahydrochloride, ficoll (type 400), ethyl aminocarbazole, herring sperm DNA (type VII), nitro blue tetrazolium (grade III), and polyvinyl pyrrolidone (PVP-40) were from Sigma Chemical Co., St. Louis, MO. Plasmids containing human globin gene sequences were provided by Dr. Sherman Weissman, Yale University. JW101 is a 0.4 kbp cDNA alpha-globin clone and pHb C6 is a 5.2 kbp genomic fragment containing the beta-globin gene in pBR322, Fukumaki, Cell, 28, 585 (1982), Plasmid pMM984 contains the complete 5.1 kb genome of the parvovirus, minute virus of mice (MVM), cloned into pBR322. This plasmid contains a single Xho I site within the MVM sequence insert. Human placental DNA was a gift from Scott Van Arsdell, Yale University.

Polymerization and Biotinylation of Intestinal Alkaline Phosphatase

Calf intestinal alkaline phosphatase was polymerized by cross-linking with disuccinimidyl suberate (DSS). The enzyme, commercially supplied as a 10 mg/ml solution, was diluted to 1 mg/ml in ice cold NMZT buffer (3M NaCl, 1 mM $MgCl_2$, 0.1 mM $ZnCl_2$, 30 nM triethanolamine, pH 7.6) in a silanized glass reaction vessel or a silanized Eppendorf tube. All subsequent reactions were done at 4° C. A 5 mg/ml solution of DSS in dimethylformamide was added (10 microl/ml of enzyme solution) in two equal aliquots (30–60 seconds apart) with gentle stirring. This solution, containing an 19-fold molar excess of DSS over enzyme, was stirred for 20 minutes during which time a coudy precipitate appeared. 10 microl aliquots of cadaverine free base (0.1 mg/ml in NMZT buffer) were added to the reaction mixture four times at 10 minute intervals. The DSS-cadaverine ratio was then made equimolar by adding another 30 microl of cadaverine solution for each ml of reaction. After stirring an additional 10 minutes, 2 microl of undiluted cadaverine-free base stock was added and the mixture stirred a further 30 minutes. The resultant clear solution was then dialyzed extensively against NMZT buffer. (The polymerization and cadaverine treatments were often repeated a second time, however these additional steps did not appear to increase the polymer size significantly since both 1X and 2X polymerized enzyme complexes detect target sequences with about equal sensitivity.)S Monomeric or polymeric forms of alkaline phosphatase were reacted with a 60-fold molar excess of biotinyl-epsilon-amino caproic acid N-hydroxysuccinimide ester (BACSE) by adding 10 microl. of a 20 mg/ml solution of BACSE (in dimethylformamide) for each mg of enzyme present in the dialysis bag. After agitating the bag on a rotary shaker at 4° C. for 2 hours, the reaction mixture was again extensively dialyzed against NMZT buffer. Sodium azide was added to a final concentration of 0.02% (W/V) and the biotinylated enzymes stored at 4° C. until use.

Preparation of Avidin-biotinylated Alkaline Phosphatase Polymer Complexes (Poly ABAP Complexes)

The biotinylated enzyme polymer was mixed with a slight excess of avidin to produce complexes capable of direct interaction with biotinylated probes hybridized on filters. The protein mixture that gave an optimal signal to noise ratio was determined emperically by analyzing the ability of various protein mixtures to discriminate between avidin-DH and biotinylated goat IgG spotted on nitrocellulose. Protein ratios were adjusted to give a strong reaction with biotinylated IgG but little, if any, signal from the avidin-DH spot. The component composition of the poly ABAP complex was further optimized for high sensitivity and specificity against Bio-16-DNA samples spotted on nitrocellulose, using a constant avidin-DH concentration and varying amounts of biotinylated enzyme polymer. The optimum protein ratios were established for each new lot of enzyme polymer to ensure maximum specificity and sensitivity. Enzyme complexes were made using avidin-DH or streptavidin and complexes made with either biotin-binding protein gave similar results.

The poly ABAP complex used was synthesized as follows: Avidin-DH (1.8 mg/ml) was diluted to a concentration of 7.2 microg./ml into AP 7.5 buffer (0.1M Tris HCl, pH 7.5, 0.1M NaCl, 2 mM $MgCl_2$, 0.05% (V/V) Triton X-100). The protein was added to a clean borosilicate glass tube prerinsed with a solution of bovine serum albumin (3%, W/V) in AP 7.5 buffer. Biotinylated alkaline phosphatase polymer (0.92 mg/ml in NMZT buffer) was then added to a final concentration of 1.8 microg/ml and complex formation allowed to proceed for at least 10 min prior to use.

EXAMPLE 1

Preparation of Dot Blots

Plasmid pMM984 DNA, either linearized by Xho I digestion or nick-translated with Bio-11 or Bio-16-dUTP substrate was serially diluted in 50 mM Tris:Cl, pH 7.5, containing 0.3N NaOH and 1.5 mg/ml of sheared herring sperm DNA. Appropriate dilutions were neutralized on ice with ice cold 3N HCl and 5 microl. aliquots spotted directly on BA-85 nitrocellulose filter sheets (Schleicher and Scheull, Keene, NH) on top of Saran wrap. Filters were air dried, baked for 4 hr at 80° C., and cut into strips containing a dilution series ranging from 0 to 128 pg of plasmid DNA per spot.

Preparation of Southern Blots

Agarose gels approximately 6 mm thick were prepared on a horizontal electrophoresis apparatus and DNA samples were electrophoresed as described by Alwine, et. al., *Methods Enzymol.*, 68, 220 (1980). DNA was transferred to nitrocellulose sheets (BA-85 or Sartorius 11336) presaturated with 20X NaCl/citrate as described by Southern and modified by Thomas, *J. Mol. Biol*, 98, 503 (1975); *Proc. Nat. Acad. Sci. USA*, 77, 5201 (1980), after performing the acid depurination step of Wahl, et. al., *Proc. Nat. Acad. Sci. USA*, 76, 3683 (1979). Complete transfer was ensured by using a 3 cm thick foam sponge saturated with 20X NaCl/Cit as a fluid reservoir beneath the gel. DNA filters were air dried, baked at 80° C. for 2-4 hr and stored at 4° C. over $CaSO_4$ until hybridized.

Hybridization Probes

Probes were prepared by nick translation essentially as described by Rigby et al., *J. Mol. Biol.*, 113, 237 (1977). Isolates of double stranded DNA to be detected were nick translated with E. Coli DNA polymerase I which catalyzes the coupling reaction of nucleotide residues to the 3' hydroxy terminus of a nick or break in the DNA strand while eliminating nucleotide residues from the 5' phosphoryl termini. The complementary DNA strand served as a template. This procedure allowed addition of labelled nucleotide residues to the double DNA strand. The strand was then denatured and each sequence served as a complement for hybridization with the native DNA strand partners in an unknown mixture.

For this process, reaction mixtures (20-200 microl.) contained 40 microg/ml DNA, 200 units/ml DNA polymerase I, 0.005 microg/ml DNAase (nicking enzyme), 50 mM TrisCl pH 7.5, 5 mM $MgCl_2$, 50 microg/ml BSA, 50 microm. each dCTP, dGTP, dATP and TTP (P-L Biochemicals, Inc., Milwaukee, WN) or Bio-dUTP analogs. Bio-4-dUTP, Bio-11-dUTP and Bio-16-dUTP were synthesized by methods according to Langer, *Proc. Nat. Acad. Sci. USA*, 78, 6633 (1981). Nick-translation reactions containing Bio-dUTP analogs were incubated for 2 hr at 14° C. while reactions with TTP were incubated for 1 hr at 14° C. Some of the Bio-dUTP reactions also contained 200 Ci/ml of alpha-$^{32}$P-dCTP (Amersham, 410 Ci/mmole). High specific radioactivity probes were prepared as above with TTP and alpha-$^{32}$P-dATP at 5 microm and 1000 Ci/mmole (Amersham).

Prehybridization and Hybridization Conditions

The general protocol outlined below was found to be optimal when using biotin-labeled hybridization probes. Filters were prehybridized for 2-4 hours at 42° C. according to Wahl et. al., *Proc. Natl. Acad. Sci. USA*, 76, 3683 (1979) in a sealed plastic bag using a mixture containing 45% (V/V) deionized formamide (conductivity 10 MHO, pH 6.5 or less), 5XNaCl Cit Denhardt's solution; *Biochem. Biophys. Res. Comm.*, 23, 641 (1966), 25 mM $NaPO_4$ buffer, pH 6.5, and sonicated herring sperm DNA (250-500 microg/ml). The hybridization buffer contained 45% (V/V) formamide, 5XNaCl Cit, 1X Denhardt's solution, 25 mM $NaPO_4$ buffer, pH 6.5, 10% dextran sulfate (added as 20% of the final volume from a 50% (W/V) stock), 250-500 g/ml sonicated herring sperm DNA and 200-500 ng/ml of a DNA probe that had been nick translated with Bio-16-dUTP. The carrier and probe DNAs were heat denatured just prior to addition. 10 ml of hybridization mixture was used per 100 $cm^2$ of filter and the hybridization reaction incubated at 42° C. (in a sealed bag) for 30-180 minutes. For analysis of single-copy mammalian gene sequences, hybridization was generally done to a Cot of $0.8 \times 10^{-2}$ (e.g., for a probe concentration of 350 ng/ml the hybridization time was 120 minutes. Following the hybridization, filters were washed 4 times at room temperature, 2-3 min for each wash, twice with 2XNaCl/Cit - 0.1% $NaDodSO_4$ and twice with 0.2X NaCl/Cit - 0.1% $NaDodSO_4$. Two stringent washes (15 min each) were done with 0.16XNaCl/Cit - 0.1% $NaDodSO_4$ at 50° C., followed by two washes at room temperature. Filters were air dried, and mounted for autoradiography with XAR X-ray film (Kodak, Rochester, NY) or assayed for biotin as described below.

Colorimetric Detection of Bio-DNA Probes

Dry nitrocellulose filter blots were incubated at 42° C. for 15 min in a 3% (W/V) solution of bovine serum albumin (BSA) in AP 7.5 buffer, air dried, baked at 80° C. for 30-60 min, and then rehydrated in the BSA - AP 7.5 buffer at 42° C. for 20-30 min. Small filter strips were treated in 13×100 mm glass tubes while larger sheets were treated in polyethylene trays or heat-sealed polypropylene bags. Filters were exposed to enzyme complexes for 5 min at room temperature; 2-5 ml of complex were used for each 100 $cm^2$ of filter. Filters were rapidly washed 3 times in 250 ml of AP 7.5 and twice in AP 9.5 (0.1M TrisHCl, pH 9.5, 0.1M NaCl, 5 mM $MgCl_2$). When avidin peroxidase (ABC) complexes were used 2X NaCl/Cit was substituted for AP 7.5 and AP 9.5 buffers.

For development with ABAP or poly ABAP complexes, filters were incubated at room temperature for 0.5 to 24 hours in AP 9.5 buffer containing 0.33 mg/ml of NBT and 0.17 mg/ml of BCIP; see *Histochemie*, 23, 1806 (1970). The phosphatase substrate solution was prepared as follows: for each 15 ml or reagent, 5 mg of NBT was suspended in 1.5 ml of AP 9.5 in a microcentrifuge tube and vortexed vigorously for 1-2 min, centrifuged briefly in a microfuge, and the supernatent decanted into 10 ml of AP 9.5 warmed to 35° in a polypropylene tube. The residual NBT pellet was extracted twice more with 1.5 ml of AP 9.5 buffer and the supernatents pooled with the original solution. The tube was rinsed with a final 0.5 ml of AP 9.5 that was also decanted into the 15 ml NBT stock solution. BCIP (2.5 mg) was dissolved in 50 micro of N,N-dimethylformamide and added dropwise with gentle mixing into the NBT solution. Care should be taken not vortex or vigorously shake the reagent mixture since this can lead to the formation of undesirable precipitates. Although this reagent was generally prepared fresh, it was stable at room temperature for at least 24 hours in the dark.

Filters were incubated with the substrate solution in sealed polypropylene bags, using 10-15 mls of solution/100 cm$^2$ of filter. To reduce nonspecific background, color development should proceed in the dark or subdued light. Single-copy mammalian gene sequences generally become visible within 30 minutes, although highly colored hybridization signals require incubation times of several hours. Color development was terminated by washing filters in 10 mM Tris HCl, 1 mM EDTA pH 7.5. Developed blots were stored dry or in heat-sealed bags containing a small amount of 20 mM Tris HCl, 5 mM EDTA, pH 9.5. Although the color intensity fades when the nitrocellulose sheet is dried, rewetting with buffer will restore color intensity as long as the filter has been stored without prolonged exposure to strong light.

Using the foregoing procedure with a known amount of DNA to be detected, and standard immunological and affinity procedures for visualizing biotin-labeled DNA, the comparative sensitivity results were determined. Serial two-fold dilutions of target (pMM984 plasmid) DNA, labeled with Bio-4dUTP, Bio-11-dUTP or Bio-16-dUTP, were mixed with a constant amount of carrier herring sperm DNA (7.5 microg) and spotted directly onto nitrocellulose strips. These strips were then incubated with various detector reagents and the sensitivity of each method determined. Results of such experiments are summarized in Table 2. Indirect immunofluorescence, using a hand-held UV-light source for visualization, was a relatively insensitive procedure with detection limits near 1 ng of target DNA (Table 2 lines 1 and 2). Indirect immunoperoxidase methods, using either DAB or EAC as a substrate, were better (Table 2 lines 3 and 4), but still only 150-200 pg were seen with a Bio-11-DNA target. The peroxidase - antiperoxidase assay method of Sternberger; Sternberger et. al., *J. Histochem. Cytochem.*, 18, 315 (1970); improved the sensitivity 2-fold over that seen with the indirect immunoperoxidase technique. However it was also not sensitive enough for the analysis of single-copy mammalian DNA sequences. With each of these immunological methods, increasing the length of the biotin "linker arm" from 4 to 11 atoms enhanced the detectability of the target by 4-fold. In contrast, Bio-4-DNA was not detected at all by complexes of avidin and biotinylated horseradish peroxidase (the ABC complexes of Hsu, Hsu, et. al., *J. Histochem. Cytochem.*, 29, 577 (1981). However, ABC complexes revealed Bio-11-DNA and Bio-16-DNA with equal efficiency and with a sensitivity limit of less than 100 pg in a simple one-step reaction (Table 2 lines 6 and 7). Complexes made with avidin-DH and biotinylated intestinal alkaline phosphatase (ABAP complexes) were even more sensitive than ABC complexes made with peroxidase (Table 2 line 10), with detection limits between 20 and 30 pg of target DNA. All attempts to increase the signal strength using multiple "sandwiching" techniques resulted in either no enhancement or a sharp decrease in signal. This was observed using either antibiotin IgG or an ABC type complex as the primary detector (Table 2, lines 8 and 9).

As shown in Table 2, line 11, the intestinal alkaline phosphatase polymer of the invention synthesized according to the foregoing procedure, which retained high levels of enzymatic activity in the complex, is termed poly ABAP. When used in conjunction with a substrate mixture of nitro blue tetrazolium and 5-bromo-4-chloro-3-indolyl phosphate, this complex detected 1-2 pg of target DNA with enzyme incubations of 3-4 hours. This level of detection is ten to fifteen-fold better than the most sensitive of the other methods.

Assuming 6-10 pg of DNA per diploid mammalian cell an average "gene" size of 5 kbp, 12 pg sensitivity would be required for analyzing unique cellular sequences in a 7.5 microg sample of DNA. The poly ABAP complex of the invention detected 1-2 pg of DNA and thus has this capacity.

TABLE 2

Relative Sensitivity of Biotin-Specific Reagents in Detecting Biotin-labeled polynucleotides bound to Nitrocellulose Filters

| Bio-DNA Target | Detector Reagents | Substrates | Detection limits (pg target sequence) |
| --- | --- | --- | --- |
| 1. Bio-4 | Anti-biotin IgG + FITC-2° Ab | — | 2000-4000 |
| 2. Bio-11 | Anti-biotin IgG + FITC-2° Ab | — | 500-1000 |
| 3. Bio-4 | Anti-Biotin IgG + HRP-2° Ab | DAB/EAC | 500-1000 |
| 4. Bio-11 | Anti-Biotin IgG + HRP-2° Ab | DAB/EAC | 150-200 |
| 5. Bio-4 | ABC (avidin DH - Bio HRP) | DAB/EAC | None detected |
| 6. Bio-11 | ABC | DAB/EAC | 75-150 |
| 7. Bio-16 | ABC | DAB/EAC | 75-150 |
| 8. Bio-16 | Anti-biotin IgG + Bio-2° Ab + ABC | DAB/EAC | 100-200 |
| 9. Bio-16 | ABC + Bio-DNA + ABC | DAB/EAC | 100-200 |
| 10. Bio-16 | ABAP (avidin-Bio Alk. Phos.) | NBT + BCIP | 20-30 |
| 11. Bio-16 | poly ABAP (avidin-poly Bio. Alk. Phos) | NBT + BCIP | 1-2 |

FIG. 1 shows typical Dot Blot assay results obtained using ABC, ABAP and poly ABAP enzyme detector complexes in the foregoing DNA detection method and incubating 60 minutes with known quantities of DNA to be detected. Peroxidase (ABC) reactions (lane 1) generally gave higher non-specific background on the nitrocellulose filters than ABAP or poly ABAP complexes (lanes 2 and 3, respectively), particularly if incubations with peroxidase substrates were longer than 30-60 minutes. However, using the poly ABAP detector, 1 pg of target DNA can be made visible without significant background noise with enzyme incubations of 3-4 hours. Since the NBT/BCIP substrate mixture did not exhibit appreciable end-product inhibition of the phosphatase activity, the intensity of the signal could be increased further by prolonging the substrate incubation period for up to 24 hours.

Having developed an enzyme complex with the capacity to detect pg quantitites of biotin-labeled DNA, the optimum conditions for using Bio-11- or Bio-16-

Figures 2A, 2B, 2C:
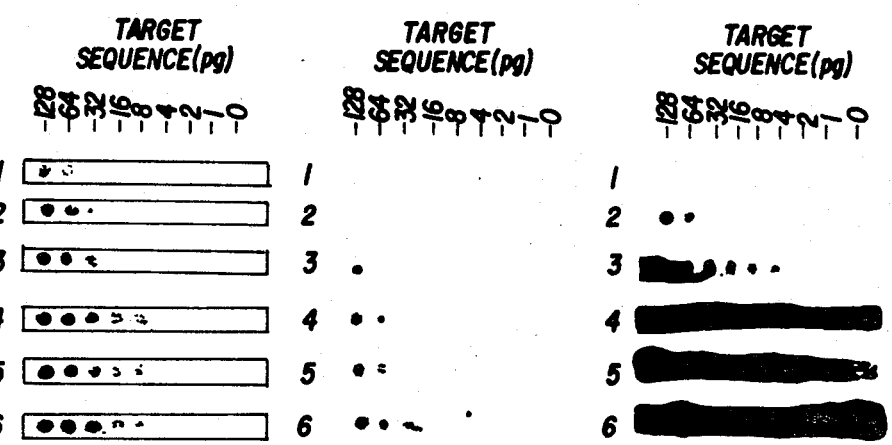
FIG. 2 shows a comparison study using biotin free DNA probes.
Figure 4A:
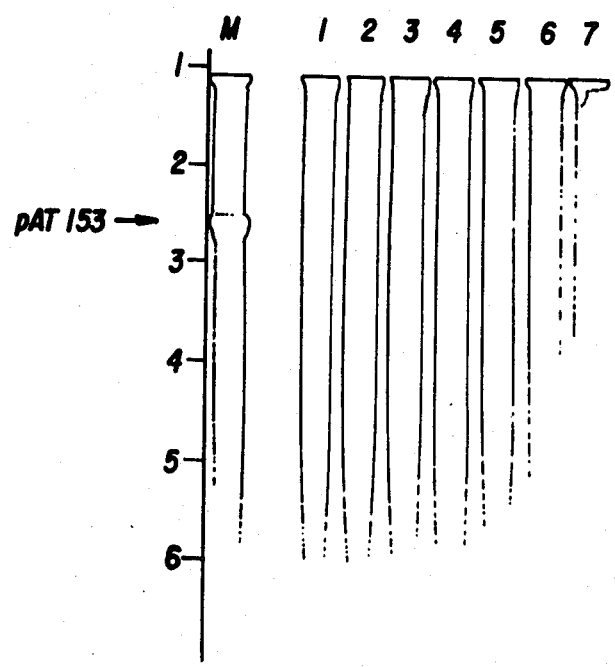
FIG. 4 shows complementary hybridization detection of human alpha and beta globin genes by the Southern Blot Method using a colorimetric visualization and visualization polymer according to the invention.
Figure 4B:
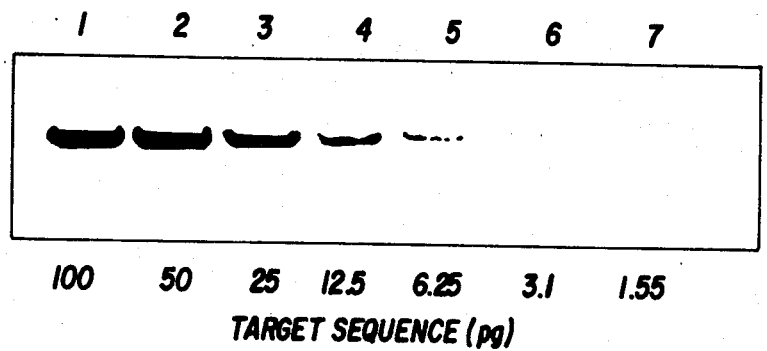

DNAs as hybridization probes were then investigated. Two pMM 984 DNA probes, one labeled with $^{32}P$ alone and the other labeled with $^{32}P$ and biotin-nucleotides, and both being probes of identical specific radioactivity, were hybridized at various probe concentrations ranging from 5 to 1000 ng/ml. The results at the various probe concentrations are shown in FIG. 2, lines 1-6; the strip numbers at the top of each graph are target concentrations. The autoradiograph of the strips hybridized with $^{32}P$-labeled DNA showed significant non-specific background at all probe concentrations above 25 ng/ml (FIG. 2C 4 days exposure of strip to film). In contrast, the autoradiograph of the strips hybridized with $^{32}P$-labeled Bio-16-DNA probe gave virtually no non-specific background noise at probe concentrations up to 750 ng/ml (FIG. 2B 4 day exposure of strip to film). This result demonstrated that a good signal to noise ratio could be obtained using very high concentrations of a Bio-DNA probe, thus making it possible to markedly reduce the hybridization times required to achieve any desired Cot value.

The coloration signal from the $^{32}P$-labeled Bio-16-DNA probe visualized with the poly ABAP complex of the invention, which was prepared according to the foregoing procedure, is shown (FIG. 2A) to be more sensitive than the autoradiograph 2B and approximately equal to 2C. This development, however, only required 4.5 hr. to complete. Accordingly, the poly ABAP complex of the invention in this test is faster than known detection methods and has high sensitivity.

Figure 3:
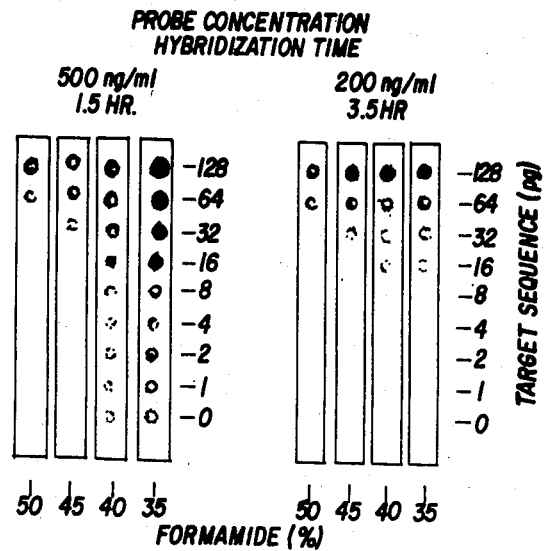
FIG. 3 shows detection of Biotin labelled DNA by the Southern Blot Method using a polyenzyme/avidin complex.

The ability of the poly ABAP detection system of the invention to visualize sequences in a Southern blot format was first analyzed in a reconstruction experiment. Various amounts of linearized pAT153 plasmid DNA were added to 10 microg. samples of sheared carrier DNA and the mixtures electrophoresed on a 1.4% agarose gel. FIG. 3A shows these 7 lanes of gel after electrophorsis and gel lane M as a marker which contained 0.6 microg of plasmid DNA stained with ethidium bromide to indicate the location of the desired plasmid bands after electrophoresis. The regions of the 7 lanes of the gel containing the 3.6 kb plasmid bands were transferred to a nitrocellulose filter and the filter hybridized with a Bio-16-labeled plasmid probe. To test critically the potential of the system, the hybridization was done under high stringency conditions (in 50% formamide) to a high Cot, conditions known to give less than maximal results. Nevertheless, after a two hour incubation in the NBT/BCIP substrate solution the poly ABAB complex clearly detected bands containing as little as 3.1 pg of plasmid DNA as shown in FIG. 3B. The intensity of the signal was also proportional to the amount of target sequence.

Detection of Specific DNA in a Mixture of DNA's

The ability of the detector system of the invention to detect specific polynucleotide sequences in an unknown mixture was demonstrated by the following procedure. Human placental DNA was digested with Eco RI, or Hind III and transferred to a nitrocellulose filter after electrophoresis in a 1% agarose gel. The DNA was then hybridized for 2 hours with Bio-16-labeled alpha-globin or Bio-16-labeled beta-globin probes. These probes were complementary for the alpha and beta globin genes (DNA) in the placental DNA. The alpha-globin probe (clone JW101) was a cDNA clone that contained only 400 nucleotides of the alpha-globin gene sequence; the beta-globin probe (pHB C6) was a 5.2 kb genomic clone FIG. 4 shows the results. Lanes 1 and 3 are ECoR1 digestions, lanes 2 and 4 are Hind III digestions, lanes 1 and 2 are hybridized with probes JW101, lanes 3 and 4 are hybridized with probe PHBC6. Lane 5 contained 750 pg each of lambda phage Hind III and PMM 984 PST1 digests in 10 microg of sheared herring DNA and was hybridized with lambda and pMM 984 probes. Restriction fragments were observed which had sizes in good agreement with the published literature; see *Proc. Nat. Acad. Sci USA*, 75, 5950 (1978); *Cell*, 19, 947 (198); *Cell* 19, 959 (1980).

All lanes were visualized by poly ABAP after several hours of enzyme incubation as shown in FIG. 4. The minor 2.5 kb Eco R1 fragment hybridized to the beta-globin probe (FIG. 4, lane 3) is most likely the Eco R1 fragment from the 540 region of the delta globin gene, which cross-hybridizes with beta-globin probes, see *Cell* supra. Although the three Hind III fragments that hybridized with the alpha-globin probe (FIG. 4, lane 2) exhibit a weaker signal than the other bands observed in lanes 1, 3 and 4, this is not surprising since each of these fragments hybridized to only a subset of the 400 nucleotides present in the probe. It is clear, however, that unique mammalian gene sequences can be visualized colorimetrically using the poly ABAP detection system. Combining Bio-DNA probes with a poly ABAP detector system thus provides a rapid and sensitive non-isotopic procedure for Southern, Northern or dot-blot hybridization analysis.

EXAMPLE 2

Comparison of Single Unit and Polymeric Enzyme Visualization

Polymers For Detecting Biotin-labeled Proteins

Application

Proteins separated by gel electrophoresis can be transferred to nitrocellulose filter sheets and specific proteins located by specific, labeled-antisera coupled with a biotin label detection system prepared according to the method described in *Proc. Natl. Acad. Sci USA*, 78, 6633 (1981). Four enzyme systems for detecting biotin-labeled antibodies were compared.

METHOD

Biotinylated goat anti-rabbit IgG (Vector Laboratories, Burlingame, CA) was serially diluted in a carrier protein solution of 0.5% w/v bovine serum albumin (Sigma Chemical Co., St. Louis, MO) in 2X SSC. A series of 8 spots containing between 0.8 and 100 pg of labeled protein, and one spot of carrier (biotin-free) protein solution were placed on filter strips. Filters were then baked at 80° C. for 1 hr. to fix the protein to the nitrocellulose strip.

Replicate strips were "blocked" by preincubating in 3% PSA in 1X AP7.5 buffer or in 2% BSA in PBS with 0.1% Triton X-100. Blocked strips were dried at 80° C. for 45 min., and rehydrated in blocking reagent for 30 min. at 42° C. The amount of biotinylated protein "target" that could be detected by each of the four avidin:biotinylated enzyme complexes was then assayed using the enzyme reactions outlined in Table 3.

TABLE 3

| Detector Complex | Enzyme | Enzyme Substrate Solution |
| --- | --- | --- |
| 1. ABC kit (Vector/ Laboratories) | horseradish | 0.2 mg/ml amino ethylcarbazole and 0.01% |

TABLE 3-continued

| Detector Complex | Enzyme | Enzyme Substrate Solution |
|---|---|---|
| | peroxidase | H$_2$O$_2$ in 50 mM NaOAc buffer, pH 5.0. |
| 2. Detek II kit (Enzo Biochem) | Same as 1 | 0.5 mg/ml diamino benzidine and 0.02% H$_2$O$_2$ in Enzo buffer. |
| 3. ABAP (monomeric) | calf intestinal alkaline phosphatase | 0.33 mg/ml Nitro Blue tetrazolium and 0.17 mg/ml bromochloroindolyl phosphate in 1X AP 9.5 buffer (2). |
| 4. poly ABAP of the invention (polymerized according to the foregoing procedure) | Same as 3 | Same as 3 |

Enzyme reactions were terminated by washing the filter strips in 10 mM TrisCl, 1 mM EDTA, pH 7.5, after 15 or 150 min. of incubation at room temperature.

The results of the four assays are as follows. Comparing the peroxidase complexes with phosphatase complexes, it was found that the peroxidase reactions were rapid, and the sensitivities of the two samples of peroxidase complex were quite different. The ABC complex could detect 13 pg in a 15 min. reaction while Detek II visualized 1.6 pg in the same amount of time. This is shown by FIG. 5A, lanes 1 and 2. This difference may be simply a function of the substrates employed.

Figure 5:
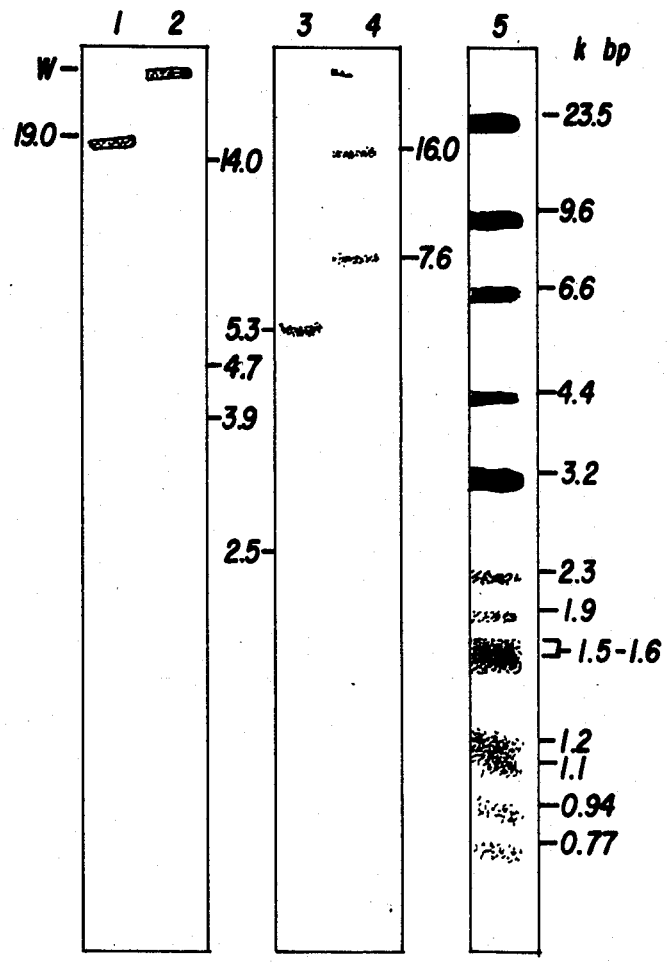
FIG. 5 shows comparative detection results produced by visualizing a biotinylated protein with an enzyme (A) and a polyenzyme (B) according to the invention.

The phosphatase complexes had similar detection capabilities in a 15 min. reaction, that is 13 pg for ABAP and 3 pg for poly ABAP. See FIG. 5, lanes 3 and 4. However, the phosphatase reactions continued to generate more signal in the course of a 2.5 hr reaction while the peroxidase reactions only increased 2-fold at best in this extended reaction, see FIG. 5B. In addition, the 2.5 hr Detek II reaction generated heavy background staining of the nitrocellulose and a false positive reaction from the carrier protein spot No. 9 (FIG. 5B, lane 2). The detection limits after 2.5 hr were 13 pg (ABC) FIG. 5B lane 1, approximately 3 pg (Deteck II FIG. 5B lane 2), 3-6 pg (ABAP; FIG. 5A, lane 3) and 0.8 pg (poly ABAP; FIG. 5B, lane 4).

The specific effect of enzyme polymerization on the sensitivity of detection is shown by comparing the FIG. 5 results of ABAP and poly ABAP detection systems after either 15 or 150 min. These incubations clearly indicate that there is an 8- to 16-fold increase in signal for the polymeric enzyme complex of the invention (FIGS. 5A and B, lanes 3 and 4).

The Utilization of Avidin-Biotinylated Alkaline Phosphatase Complexes in Immunocytochemical Detection of Human Chorionic Gonadotophin A comparison study was undertaken to determine the usefulness of biotinylated polymers of alkaline phosphatase in immunocytochemistry. The avidin-biotinylated polymers of alkaline phoshatase method (poly ABAP) was compared to the peroxidase anti-peroxidase (PAP) technique of Sternberger, Sternberger et. al., *J. Histochem., Cytochem.*, 18, 3156 (1970).

Tissue sections from cancerous organs containing human chorionic gonadotropin were prepared on slides as follows:

Sections were dewaxed in Xylene twice for 5 min. each, then hydrated to distilled water through graded alcohols. Sections for peroxidase anti-peroxidase (PAP) technique were treated with 1.5% H$_2$O in P.B.S. for 30 min. to block endogenous peroxidase. Sections for ABAP technique were oarried to the next step without treatment.

The sections were treated with the following suppressor systems:

For the PAP technique the sections were treated with 10% Normal Swine Serum in 3% BSA in 0.05M Tris. HCl buffer ph 7.5 for 20 min.

For the polyABAP technique, the sections were treated only with 3% BSA in 0.05M Tris.HCl buffer pH 7.5 for 20 min. The sections were taken mounted on slides.

Primary antibody (Rabbit anti-HCG, Accurate Chem and Scientific Corp) was diluted from 1:1000 to 1:1,000,000 in Tris.HCl buffer pH 7.5 and applied to the slides both for 1 hour at room temp. and overnight in a wet chamber at room temperature. The slides were washed three times with TrisHCl buffer pH 7.5.

Secondary Serum was then added.

For the PAP technique, a 1:20 dilution of Swine anti Rabbit antiserum (Accurate Chemical and Scientific Corp.) was applied to the tissue section for a half hour at room temperature. For the poly ABAP technique, a 1:400 dilution of biotinylated goat anti-rabbit antiserum (Vector Laboratories, Inc.) diluted in Tris.HCl buffer pH 7.5 was applied for one half hour at room temp. In addition biotin labelled swine anti-rabbit antiserum was prepared and applied to the tissue sections in separate runs. Slides were then washed three times in Tris HCl buffer for 5 min. each.

The Detection System was then added. For the PAP system, a 1:50 dilution of rabbit PAP was prepared in Tris HCl buffer and applied to the slides for one hour at room temperature. For the polyABAP system, 20 ul. of avidinDH was added to a borosilicate glass test tube containing 2.5 ml. of Tris HCl buffer pH 7.5 2.5 ul. of polymerized alkaline phosphatase was added and the mixture allowed 5 min to complex. The complex was then applied to the slides for one hour at room temperature. The slides were washed three times at room temp in Tris HCl Buffer pH 7.5.

The development system was then added. For the PAP technique, slides were developed in diaminobenzidine tetrahydrochloride and H$_2$O$_2$. For the polyABAP technique, slides were developed in Napthol AS Phosphate and Fast Red TR Salt diluted in 0.05M Tris HCl buffer pH 9.5 in 0.1M NaCl with 50 mM MgCl$_2$ for 20 min. at room temp.

The slides were mounted and coverslipped and examined by light microscopy.

Figure 7:
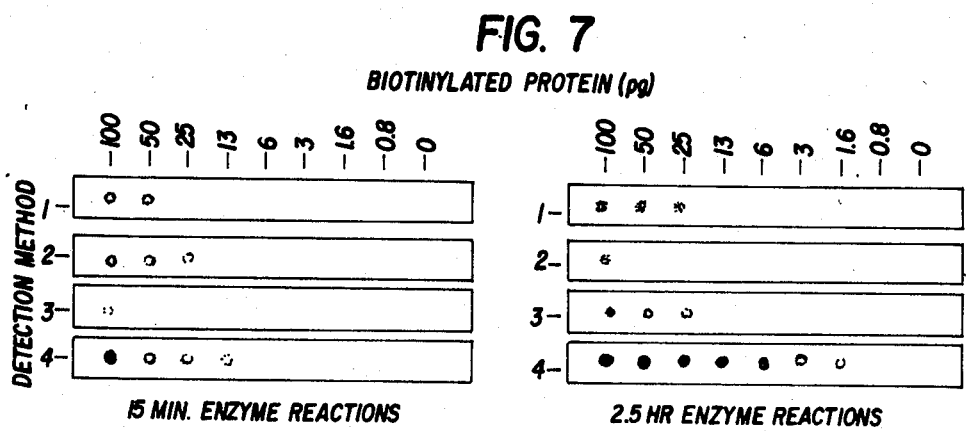
FIG. 7 shows the results of the poly ABAP technique for detection of protein according to the invention.
Figure 6B:
FIG. 6 shows the results of a PAP detection technique for detection of protein.
Figure 6A:
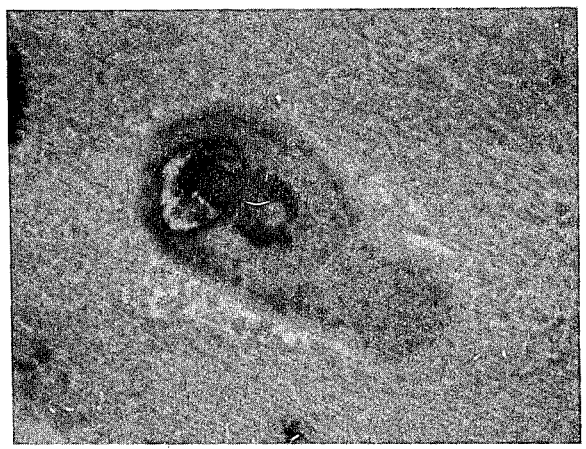

The results are illustrated in FIGS. 6 and 7 as pictures of the slides.

FIG. 6 shows the results of the PAP technique at 1:16,000 dilution.

FIG. 7 shows the results of the polyABAP technique at 1:160,000 dilution.

It has been found that with overnight incubations and depending upon the primary antibody, the polyABAP technique of the invention is 4 to 20 times more sensitive than PAP. At short primary antibody incubations of one hour, the technique of the invention is 4 to 6 times more sensitive. The increased sensitivity noted in overnight incubations is related to the ability of the polyABAP technique to increase its sensitivity while the PAP method remains at about the original titer.

What is claimed is:

1. A visualization polymer comprising essentially identical multiple visualization units each having at least one visualization site;
   said visualization units being directly bonded together though chemical groups or backbone moieties of adjacent said visualization units, or linked by a coupling agent covalently bonded to chemical groups or backbone moieties of adjacent said visualization units,
   said visualization unit being an enzyme, wherein the enzymatic site is the visualization site, a tagged natural or synthetic polypeptide, a tagged polyol, a tagged polyolefin or a tagged polycarbohydrate wherein the tag of the tagged polypeptide, tagged polyol, tagged polyolefin or tagged polycarbohydrate is the visualization site thereof;
   said chemical group being an amine group, an oxidized 1,2-diol group, a carboxyl group, a mercaptan group, a hydroxy group or a carbon-hydrogen bond;
   said backbone moiety being an amide bond, a carbon-carbon bond, a carbon-oxygen bond or a carbon-hydrogen bond; and said chemical group or backbone moiety being located at a position which is at least one atom away from the visualization site of said visualization unit;
   said coupling agent being derived from a bi- or multi-(homo- or hetero-) functional organic cross-linking reagent of the formula

wherein A, B and E are independently selected from the group consisting of hydrogen, a carboxylic acid group, an acid halide group, an activated ester, a mixed anhydride, an acyl imidazole, an N-(carbonyloxy)imide group, an iminoester, a primary amine, an aldehyde group, an alphahalomethylacarbonyl group, a hydrazine group, an acylhydrazide group, an azide group and an N-maleimide group; at least two of A, B and E are other than hydrogen; and $R^1$ is an aliphatic group of at least two carbons or an aromatic group of at least six carbons; and
   the tag of said tagged polypeptide, tagged polyol, tagged polyolefin or tagged carbohydrate is a fluorescent group, a dye, a radioactive group, a photon emitter or an electron dense group.

2. A visualization polymer according to claim 1 wherein the visualization unit is an enzyme selected from the group consisting of peroxidase, galactosidase, luciferinase, glucose oxidase, acid phosphatase or alkaline phosphatase.

3. A visualization polymer according to claim 1 wherein the cross-linking reagent is an aliphatic-1, omega-diacyloxy disuccinimide having from 4 to 20 carbons in the aliphatic group.

4. A visualization polymer according to claim 1 wherein said visualization units are directly bonded together through oxidative cross-linking using an oxidative enzyme.

5. A visualization polymer according to claim 4 wherein the oxidative enzyme is horseradish peroxidase.

6. A visualization polymer according to claim 1 wherein the visualization unit is horseradish peroxidase or alkaline phosphatase.

7. A visualization polymer according to claim 6 wherein the visualization units are linked by a coupling agent derived from disuccinimidyl suberate which bonds with epsilon amine groups.

8. A visualization polymer according to claim 6 wherein the visualization unit is peroxidase and the visualization units are coupled by a coupling agent derived from tri(lysyl)lysine which bonds with oxidized 1,2-diol groups.

9. A detection-visualization composition comprising a detecting agent carrying a visualization polymer as described according to claim 1, said detecting agent being an antibody, a lectin, avidin, streptavidin, a DNA repressor protein, a hormone, a stereo-specific receptor protein, a high affinity enzyme, a sequence specific polynucleotide binding protein or a complementary polynucleotide sequence.

10. A detection-visualization composition according to claim 9 wherein said detecting agent carries said visualization polymer through an intermediate ligand binding complex comprising a first ligand covalently bonded to said detecting agent, a ligand binding compound and a second ligand covalently bonded to said visualization polymer; said detecting agent, said ligand binding compound and said visualization polymer forming a complex with said first and second ligands functioning as ligands to said ligand binding compound.

11. A composition according to claim 9 wherein said detecting agent is an antibody, a lectin or a complementary polynucleotide sequence, said ligand binding compound is avidin or streptavidin, and said first and second ligands are independently selected from N-(omega acyl) amido(biotin or iminobiotin), said omega acyl group being of from about 2 to 20 carbons in length; or an N-(omega-oligomer)amido(biotin or imido biotin) wherein the omega-oligomer is a polyol, a polyamide or a polyvinyl group of from about 2 to 30 units in length; or N-(omega alkenyl)amido (biotin or iminobiotin), said omega alkenyl group being about 3 to 20 carbons in length.

12. A detection kit for analysis of target molecules in a biological material comprising a metered quantity of a detection agent-visualization polymer composition as described according to claim 9.

13. A detection-visualization composition according to claim 9 wherein said visualization polymer is bonded or complexed directly with said detecting agent.

14. A composition according to claim 13 wherein said detecting agent is covalently bonded to said visualization polymer with a linking group derived from a bi- or multi-(homo or hetero) functional organic cross-linking reagent.

15. A visualization polymer complex comprising a visualization polymer according to claim 1 covalently bonded to a ligand, and a ligand binding compound associated with said ligand.

16. A visualization polymer complex according to claim 15 wherein the ligand binding compound is a lectin, avidin, streptavidin, a high affinity enzyme, a sequence specific polynucleotide binding protein or a complementary polynucleotide sequence.

17. A visualization polymer complex according to claim 15 wherein the ligand binding compound is a lectin, avidin or streptavidin.

18. A visualization polymer complex according to claim 17 wherein the ligand binding compound is lectin and the ligand is a sugar bound to the visualization through a bi- or multi-(homo or hetero) functional organic cross-linking reagent.

19. A visualization polymer complex according to claim 17 wherein the ligand binding compound is avidin or streptavidin and the ligand is an N-(omega acyl)amino(biotin or iminbiotin), said omega acyl group being of from about 2 to 20 carbons in length; or an N-(omega-oligomer)amido(biotin or iminobiotin); said omega-oligomer being a polyol, a polyamide or a polyvinyl group of from about 2 to 30 units in length.

20. A visualization polymer complex according to claim 19 wherein the ligand is N-(omega acyl)amido(biotin or iminobiotin).

21. A detection kit for analysis of target molecules in a biological material comprising metered quantities of a buffered, aqueous solution of a detection agent component and a buffered, aqueous solution of a visualization polymer complex component and a standardized quantity of an aqueous mixture of said visualization polymer, said detection agent component and said visualization polymer complex component being capable of associating when combined, said visualization polymer complex component comprising a visualization polymer covalently bonded to a ligand, and a ligand binding compound associated with said ligand;

said visualization polymer comprising essentially identical multiple visualization units each having at least one visualization site; said visualization units being directly bonded together through chemical groups or backbone moieties of said visualization units, or linked by a coupling agent covalently bonded to chemical groups or backbone moieties of said visualization units;

said visualization unit being an enzyme, wherein the enzymatic site is the visualization site, a tagged natural or synthetic polypeptide, a tagged polyol, a tagged polyolefin or a tagged polycarbohydrate wherein the tag of the tagged polypeptide, tagged polyol, tagged polyolefin or tagged polycarbohydrate is the visualization site thereof, said chemical group being an amine group, an oxidized 1,2-diol group, a carboxy group, a mercaptan group, a hydroxy group or a carbon-hydrogen bond;

said backbone moiety being an amide bond, a carbon-carbon bond, a carbon-oxygen bond or a carbon-hydrogen bond;

said chemical group or backbone moiety being located at a position which is at least one atom away from the visualization site of said visualization unit;

said coupling agent being derived from a bi- or multi- (homo-or hetero-) functional organic cross-linking reagent of the formula

wherein A, B and E are independently selected from the group consisting of hydrogen, a carboxylic acid group, an acid halide group, an activated ester, a mixed anhydride, an acyl imidazole, an N-(carbonyloxy)imide group, an iminoester, a primary amine, an aldehyde group, an alphahalomethylcarbonyl group, a hydrazine group, an acylhydrazide group, an azide group and an N-maleimide group; at least two of A, B and E are other than hydrogen; and $R^1$ is an aliphatic group of at least two carbons or an aromatic group of at least six carbons; and the tag of said tagged polypeptide, tagged polyol, tagged polyolefin or tagged carbohydrate is a fluorescent group, a dye, a radioactive group, a photon emitter or an electron dense group.

22. A kit according to claim 21 wherein said detecting agent is an antibody, a lectin, avidin, streptavidin, a DNA repressor protein, a hormone, a stereospecific receptor protein, a high affinity enzyme, a sequence specific polynucleotide binding protein or a complementary polynucleotide sequence.

23. A method for visualizing the presence of an inorganic or organic target molecule in a biological material, which comprises:

combining said target with a detecting agent with carries a visualization polymer comprising essentially identical multiple visualization units directly bonded together or linked by a coupling agent through chemical groups or backbone moieties of said visualization units;

said visualization unit having at least one visualization site and said visualization unit being an enzyme wherein the enzymatic site is the visualization site, a tagged natural or synthetic polypeptide, a tagged polyol, a tagged polyolefin or a tagged polycarbohydrate wherein the tag of the tagged polypeptide, the tagged polyol, the tagged polyolefin or the tagged polycarbohydrate is the visualization site thereof, said chemical group being an amine group, an oxidized 1,2-diol group, a carboxy group, a mercaptan group, a hydroxy group or a carbon-hydrogen bond;

said chemical group or backbone moiety being located within said visualization unit at a position which is at least one atom away from the visualization site of said visualization unit;

said coupling agent being derived from a reactive bi- or multi- homo- or hetero-functional organic cross-linking reagent of the formula

wherein A, B and E are independently selected from the group consisting of hydrogen, a carboxylic acid group, an acid halide group, an activated ester, a mixed anhydride, an acyl imidazole, an N-(carbonyloxy)imide group, an iminoester, a primary amine, an aldehyde group, an alphahalomethylcarbonyl group, a hydrazine group, an acylhydrazide group, an azide group and an N-maleimide group; at least two of A, B and E are other than hydrogen; and $R^1$ is an aliphatic group of at least two carbons or an aromatic group of at least six carbons; and the tag of the tagged polypeptide, tagged polyol, tagged polyolefin or tagged carbohydrate is a fluorescent chemical group, a dye, a radioactive group, a photon emitter or an electron dense moiety.

24. A method according to claim 23 wherein the chemical group is a mercaptan and the cross-linking reagent forms sulfide bonds using an alphahalomethylcarbonyl group or an N-maleimide group.

25. A method according to claim 23 wherein said detecting agent is an antibody, a lectin, a DNA repressor protein, avidin, streptavidin, a hormone, a stereospecific receptor protein, a high affinity enzyme, a sequence specific polynucleotide binding protein, or a complementary polynucleotide sequence.

26. A method according to claim 23 wherein said molecule target is produced by or has an effect upon a biological organism.

27. A method according to claim 26 wherein said molecule target is a protein, a lipid, a carbohydrate, a hormone, a steroid, a polynucleotide, a nucleic acid, a nucleoprotein, a nucleoside, a nucleotide, a purine or pyrimidine base, a drug, a sugar, a carcinogen, an antibiotic, a haptene, an antigen, a heavy metal, an organometallic compound, a metal-protein complex or a toxic inorganic salt.

28. A method according to claim 23 wherein the chemical group is a 1,2-diol group which is oxidized to a dialdehyde group and the cross-linking reagent forms hydrazone, amide, acylhydrazide or imine bonds with said dialdehyde group.

29. A method according to claim 28 wherein the chemical groups are epsilon or primary amino groups which form amide bonds with the cross-linking reagent.

30. A method according to claim 29 wherein said visualization unit is peroxidase, luciferase, glucose oxidase, galactoxidase, acid phosphatase or alkaline phosphatase.

31. A method according to claim 23 wherein the visualization polymer is bonded to the detecting agent by an organic bivalent linking group.

32. A method according to claim 31 wherein the organic bivalent linking group is dervied from a bi- or multi- homo- or hetero-functional organic cross-linking reagent.

33. A method according to claim 31 wherein the detecting agent is an antibody, lectin, avidin, steptavidin, a DNA repressor protein, a hormone, a stereospecific receptor protein, a high affinity enzyme, a sequence specific polynucleotide binding protein or a complementary polynucleotide sequence.

34. A method according to claim 23 wherein said detecting agent carries said visualization polymer through an intermediate ligand binding complex comprising a first ligand covalently bonded to said detecting agent, a second ligand covalently bonded to said visualization polymer and a ligand binding compound wherein said first and second ligands are complexed with said ligand binding compound.

35. A method according to claim 34 wherein said ligand binding compound is an antibody, lectin, avidin, streptavidin, a high affinity enzyme, a sequence specific polynucleotide binding protein or a complementary polynucleotide sequence.

36. A method according to claim 34 wherein the detecting agent is a lectin, the ligand binding compound is avidin or streptavidin, and the first and second ligands are independently selected from N-(omega acyl)amido(biotin or iminobiotin), said omega acyl group being of 4 to 20 carbons; or an N-(omega-oligomer) amido(biotin or iminobiotin) wherein the omega-oligomer is a polyol, a polyamide or a polyvinyl group of from 2 to 30 units.

37. A method according to claim 36 wherein the molecular ratio of visualization polymer to avidin or streptavidin is about 3 to 1.

38. A method according to claim 34 wherein the detecting agent is an antibody, the ligand binding compound is avidin or streptavidin, and the first and second ligands are independently selected from N-(omega acyl)amido(biotin or iminobiotin), said omega acyl group being of from 4 to 20 carbons; or an N-(omega-oligomer)amido(biotin or iminobiotin) wherein the omega-oligomer is a polyol, a polyamide or polyvinyl group of 2 to 30 units in length.

39. A method according to claim 38 wherein a first target-specific antibody is used to detect said target molecule and form a target/first antibody conjugate, a second antibody having said biotin label ligand and being general for said first antibody is incubated with said conjugate and said visualization polymer is complexed with said second antibody through said first and second ligands and said ligand binding compound.

40. A method according to claim 38 wherein the molecular ratio of visualization polymer to avidin or streptavidin is about 3 to 1.

41. A method according to claim 34 wherein said detecting agent is a complementary polynucleotide sequence.

42. A method according to claim 41 wherein said compound is an antibody, lectin, avidin, streptavidin, or a high affinity enzyme.

43. A method according to claim 41 wherein said compound is lectin and said first and second ligands are binding sugars.

44. A method according to claim 41 wherein said compound is avidin or streptavidin and said first and second ligands are independently selected from N-(omega acyl)amido(biotin or iminobiotin), said omega acyl group being of from 4 to 20 carbons; or an N-(omega-oligomer)amido(biotin or iminobiotin) wherein the omega-oligomer is a polyol or polyamide or polyvinyl group of 2 to 30 units in length, or N-(alkenyl)amido(biotin or iminobiotin) having from 3 to 20 carbons in the alkenyl group.

45. A method according to claim 44 wherein the molecular ratio of visualization polymer to avidin or streptavidin is about 3 to 1.

* * * * *

UNITED STATES PATENT AND TRADEMARK OFFICE
CERTIFICATE OF CORRECTION

PATENT NO. : 4,687,732
DATED : August 18, 1987
INVENTOR(S) : Ward et al.

It is certified that error appears in the above-identified patent and that said Letters Patent is hereby corrected as shown below:

At column 3, lines 29-30, "flexability" should be --flexibility--

At column 4, line 10, "practise" should be --practice--

At column 6, line 34, "or and" should be --or an--

At column 7, line 60, "suifide" should be --sulfide--

At column 9, line 26, delete "an" second occurrence

At column 9, line 49, delete "monomer"

At column 10, lines 16-17, "semi-emperic" should be --semi-empiric--

At column 10, line 49, "semi-emperic" should be --semi-empiric--

At column 11, line 5, "emperic" should be -- empiric--

At column 11, line 29, "reversably" should be --reversibly--

At column 11, line 68, "suseptible" should be -- susceptible--

UNITED STATES PATENT AND TRADEMARK OFFICE
CERTIFICATE OF CORRECTION

PATENT NO. : 4,687,732

DATED : August 18, 1987

INVENTOR(S) : Ward et al.

It is certified that error appears in the above-identified patent and that said Letters Patent is hereby corrected as shown below:

At column 12, line 3, "adacent" should be -- adjacent --

At column 13, line 7, "$-(CH_2-C_6H_4-(CH_2)m-$" should be -- $-(CH_2)_1-C_6H_4-(CH_2)_m-$ --

At column 18, line 62, "emperic" should be --empiric--

At column 23, line 41, "1879" should be --1979--

At column 24, line 11, "coudy" should be --cloudy--

At column 24, line 26, delete "S"

At column 24, line 46, "emperically" should be --empirically--

At column 30, line 11, "(198)" should be --(1980)--

At column 30, line 12, "polv" should be --poly--

At column 30, line 16, "540" should be --5'--

At column 31, line 20, "TrisCl" should be --Tris HCl--

At column 31, line 42, "Deteck" should be --Detek--

At column 32, line 3, "orried" should be --carried--

UNITED STATES PATENT AND TRADEMARK OFFICE
CERTIFICATE OF CORRECTION

PATENT NO. : 4687,732

DATED : August 18, 1987

INVENTOR(S) : Ward et al.

It is certified that error appears in the above-identified patent and that said Letters Patent is hereby corrected as shown below:

At column 33, lines 42-43, "alphahalomethylacarbonyl" should be --alphahalomethylcarbonyl--

At column 35, line 9, "amino" should be --amido--

At column 36, line 21, "with" should be --which-- (2nd occurrence)

At column 37, line 38, "dervied" should be --derived--

Signed and Sealed this

Twenty-third Day of January, 1990

Attest:

JEFFREY M. SAMUELS

*Attesting Officer*       *Acting Commissioner of Patents and Trademarks*

UNITED STATES PATENT AND TRADEMARK OFFICE
CERTIFICATE OF CORRECTION

PATENT NO. : 4,687,732
DATED : 8/18/87
INVENTOR(S) : David Ward et al.

It is certified that error appears in the above-identified patent and that said Letters Patent is hereby corrected as shown below:

Column 1, line 3, insert the following:

The invention identified above is a subject invention under 35 U.S.C. 200, et seq., and the Standard Patent Rights Clause at 37 C.F.R. 401.14 or F.A.R. 52.227-11, which are included among the terms of the grant/contract award from the Public Health Service/National Institutes of Health.

Signed and Sealed this

First Day of June, 1999

Attest:

Attesting Officer

Q. TODD DICKINSON

Acting Commissioner of Patents and Trademarks